United States Patent [19]

Cantrell et al.

[11] Patent Number: 5,159,081
[45] Date of Patent: Oct. 27, 1992

[54] INTERMEDIATES OF PERIPHERALLY SELECTIVE N-CARBONYL-3,4,4-TRI-SUBSTITUTED PIPERIDINE OPIOID ANTAGONISTS

[75] Inventors: Buddy E. Cantrell, Fountaintown; Dennis M. Zimmerman, Mooresville, both of Ind.

[73] Assignee: Eli Lilly and Company, Indianapolis, Ind.

[21] Appl. No.: 677,708

[22] Filed: Mar. 29, 1991

[51] Int. Cl.$^5$ .......................................... C07D 211/16
[52] U.S. Cl. ................................... 546/226; 546/207; 546/231; 546/232; 546/233; 546/235
[58] Field of Search ................................ 546/226, 232

[56] References Cited

U.S. PATENT DOCUMENTS

| | | | |
|---|---|---|---|
| 3,936,468 | 2/1976 | Yamamoto et al. | 260/293.8 |
| 3,991,199 | 11/1976 | Berger | 424/267 |
| 4,081,450 | 3/1978 | Zimmerman | 260/293.67 |
| 4,115,400 | 9/1978 | Zimmerman | 260/326.5 |
| 4,141,980 | 2/1979 | Berger | 424/256 |
| 4,175,197 | 11/1979 | Zimmerman | 546/339 |
| 4,191,771 | 3/1980 | Zimmerman | 424/267 |
| 4,284,635 | 8/1981 | Zimmerman | 424/267 |
| 4,581,456 | 4/1986 | Barnett | 546/185 |
| 4,663,460 | 5/1987 | Barnett | 546/334 |
| 4,891,379 | 1/1990 | Zimmerman et al. | 514/315 |
| 4,992,450 | 2/1991 | Zimmerman et al. | 514/315 |

OTHER PUBLICATIONS

"New Structural Concepts for Narcotic Antagonist Defined in a 4-Phenylpiperidine Series", of Zimmerman, et al., Nature, 275, No. 5678, pp. 332-334 (1978).

"Selective Opioid Receptor Agonist and Antigonist; Research Tools and Potential Therapeutic Agents", J. Med. Chem., 1990, 33, 895-902 of Zimmerman, et al.

Leander, et al., in the paper "Novel phenylpiperidine Opioid Antagonist and Partial Antagonists; Effects on Fluid Consumption", European Journal of Pharmacology, 81, 185-192 (1982).

Oh-ishi, et al., Journal of Medicinal Chemistry, 1973, vol. 16, 12, 1376-1378.

Leander, et al., in the paper entitled "Antagonism of Bremazocine-Induced Urination as a Test for Kappa-Opioid Receptor Antagonists Within the Phenylpiperidine Series", Drug Development Research, 4, 421-427 (1984).

Baile, et al., in a paper entitled "Opiate Antagonists and Agonists and Feeding in Sheep", Philsiology and Behavior, 26, 1019-23 (1981).

Leander in a paper entitled "A Kappa Opioid Affect; Increased Urination in the Rat", The Journal of Pharmacology and Therapeutics, 224, No. 1, 89-94 (1983).

*Primary Examiner*—Mukund J. Shah
*Assistant Examiner*—Jyothsna Venkat
*Attorney, Agent, or Firm*—Joseph A. Jones; Leroy Whitaker; David E. Boone

[57] ABSTRACT

Intermediates of N-carbonyl-3,4,4-substituted piperidines are provided which are useful in the preparation of peripheral opioid antagonists.

18 Claims, No Drawings

INTERMEDIATES OF PERIPHERALLY SELECTIVE N-CARBONYL-3,4,4-SUBSTITUTED PIPERIDINE OPIOID ANTAGONISTS

FIELD OF THE INVENTION

This invention relates to certain N-substituted piperidines and their use as peripherally selective opioid antagonists.

BACKGROUND OF THE INVENTION

A substantial body of evidence indicates that peripheral opioid peptides and their receptors have a major physiological role in the regulation of gut motility. Consequently gastrointestinal disorders such as idiopathic constipation and irritable bowel syndrome may relate to a dysfunction of opioid receptor mediated control and agents which act as antagonists for these receptors may benefit a patient suffering from such a dysfunction.

Natural and synthetic opiates such as morphine have been used extensively in the mediation of pain. However, these agents can produce undesirable side effects such as constipation, nausea, and vomiting which are peripheral to the desired action as analgesics. Thus, a peripheral opioid antagonist should not substantially affect the analgesic effects of the opiate while acting to control gastrointestinal function and to minimize the undesirable side effects of the narcotic drug.

A number of opioid antagonists have been reported including naloxone and naltrexone (Blumberg et al., *Toxicol. Appl. Pharmacol.*, 10, 406, 1967). Other derivatives of these compounds have been recently reported (Portoghese et al., *J. Med. Chem.*, 31, 281-282, 1988). 4-Arylpiperidines have also been reported as having analgesic activity and in some instances acting as narcotic antagonists. Zimmerman, U.S. Pat. No. 4,191,771 (1980); Barnett, U.S. Pat. No. 4,581,456 (1986); Zimmerman, U.S. Pat. No. 4,081,450 (1978). These compounds are disclosed as having useful analgesic activity and in some cases acting as potent narcotic antagonists.

It would be advantageous to have compounds which would act as antagonists to the peripheral effects of opiate analgesics and endogenous opioid peptides. It would also be advantageous if these compounds had a minimal effect on the analgesic activity of the opiate drugs. It would be further advantageous to have compounds which can act to minimize the effects of idiopathic constipation and irritable bowel syndrome.

It has now been found that the N-substituted piperidines of the instant invention are useful as peripherally selective opioid antagonists. The instant compounds are useful in preventing peripherally mediated, undersired opiate effects and in relieving the symptoms of idiopathic constipation and irritable bowel syndrome. Certain of the instant compounds are also useful as intermediates in preparing new piperidine compounds.

SUMMARY OF THE INVENTION

The present invention relates to a trans-3,4-isomer of a compound of Formula I wherein:

$R^1$ is H or $(C_1-C_5)$alkyl;

$R^2$ is H, $C_1-C_5$)alkyl, or $(C_2-C_6)$alkenyl;

$R^3$ is H, $(C_1-C_{10})$alkyl, $(C_3-C_{10})$alkenyl, $(C_3-C_8)$-cycloalkyl, $(C_3-C_8)$ cycloalkyl-$(C_1-C_3)$ alkyl, phenyl, $(C_5-C_8)$ cycloalkenyl, $(C_5-C_8)$cycloalkenyl-$(C_1-C_3)$alkyl, or phenyl-$(C_1-C_3)$ alkyl.

$R^4$ is H, $(C_3-C_8)$ cycloalkyl, $(C_1-C_{10})$ alkyl, $(C_3-C_{10})$alkenyl, $(C_3-C_8)$cycloalkyl-$(C_1-C_3)$alkyl, phenyl or phenyl-$(C_1-C_3)$ alkyl.

$R^5$ is H, $(C_1-C_{10})$alkyl, $(C_1-C_{10})$alkanoyl, C(O)-CH—[(CH$_2$)$_3$NHC(NH)NHNO$_2$]NHC(O)W, C(O)NH(C$_1$-C$_{10}$)alkyl, [C(O)(C$_2$)$_m$C(O)]$_q$R$^6$, or [C(O)(CH$_2$)$_m$NHC(O)]$_q$R$^6$;

W is $(C_1-C_{10})$alkyl, $O(C_1-C_{10})$alkyl, $(C_1-C_4$ alkyl)NHC(O)(C$_1$-C$_6$)- alkyl, or $(C_1-C_4$ alkyl)-C(O)NHB, where B is $(C_1-C_{10})$- alkyl, phenyl or phenyl-$(C_1-C_3)$alkyl;

$R^6$ is OR$^7$, NHR$^7$, OCH$_2$C(O)NR$^8$R$^9$, O(C$_1$-C$_4$alkyl)OC(O)R$^{10}$, $(C_1-C_{10})$alkyl, or NHCHR$^{11}$C(O)R$^{12}$;

$R^7$ is H, $(C_1-C_{10})$alkyl, $(C_3-C_8)$cycloalkyl, $(C_3-C_8)$cycloalkyl-$(C_1-C_3)$ alkyl or (CH$_2$)$_m$C(O)NR$^8$R$^9$;

$R^8$ is H, or $(C_1-C_{10})$alkyl;

$R^9$ is H, or $(C_1-C_{10})$alkyl;

$R^{10}$ is $(C_1-C_{10})$alkyl, $C_3-C_8$)cycloalkyl, or $R^{11}$ is H, $(C_1-C_{10})$alkyl, or phenyl-$(C_1-C_3)$alkyl;

$R^{12}$ is OR$^{13}$ or NR$^{13}$R$^{14}$;

$R^{13}$ is H or $(C_1-C_{10})$alkyl;

$R^{14}$ is H or $(C_1-C_{10})$alkyl;

n=1-3;

m=1-3;

q=1-3; and the pharmaceutically acceptable salts thereof.

The present invention also provides methods of employing, and pharmaceutical formulations containing, a compound of the invention.

The present invention further provides trans-3,4-isomers of the intermediates of Formula II

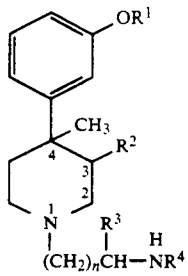

IIa wherein:
$R^1$ is hydrogen or $(C_1-C_5)$ alkyl;
$R^2$ is hydrogen, $(C_1-C_5)$ alkyl, or $(C_2-C_6)$ alkenyl;
$R^3$ is hydrogen, $(C_1-C_{10})$ alkyl, $(C_3-C_8)$cycloalkyl, $C_3-C_{10}$ alkenyl, $(C_3-C_8)$cycloalkyl-$(C_1-C_3)$alkyl, phenyl, $(C_5-C_8)$cycloalkenyl, $(C_5-C_8)$cycloalkenyl-$(C_1-C_3)$alkyl, or phenyl-$(C_1-C_3)$alkyl;
$R^4$ is hydrogen, $(C_3-C_8)$ cycoalkyl, $(C_1-C_{10})$ alkyl, $C_3-C_{10}$ alkenyl, $(C_3-C_8)$cycloalkyl-$(C_1-C_3)$alkyl, phenyl or phenyl-$(C_1-C_3)$alkyl; and
$n=1-3$.

In another embodiment the instant invention provides compounds of Formula IIb which are intermediates in the preparation of Formula IIa compounds

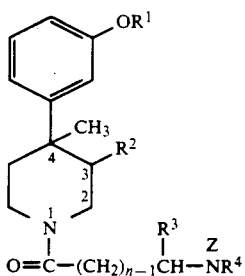

IIb wherein $R^1$, $R^2$, $R^3$, $R^4$ and n are as defined above and Z is hydrogen when $R^4$ is phenyl or an amino blocking group when $R^4$ is other than phenyl.

DETAILED DESCRIPTION OF THE INVENTION

The term "$(C_1-C_{10})$ alkyl," as used herein, represents a branched or linear alkyl group having from one to ten carbon atoms. Typical $C_1-C_{10}$ alkyl groups include methyl, ethyl, n-propyl, iso-propyl, butyl, iso-butyl, sec-butyl, tert-butyl, pentyl n-hexyl, iso-hexyl, and the like. The terms "$(C_1-C_3)$ alkyl" and "$(C_1-C_5)$alkyl" similarly is a linear or branched alkyl group having one to three and one to five carbon atoms respectively.

The term "$(C_3-C_8)$ cycloalkyl" represents cyclopropyl, cyclobutyl, cyclopentyl, cyclohexyl, cycloheptyl and cyclooctyl.

The term "$(C_3-C_8)$ cycloalkyl-$(C_1-C_3)$ alkyl" represents a linear $C_1-C_3$ alkyl chain substituted at a terminal carbon with a $(C_3-C_8)$ cycloalkyl group. Typical alkylcycloalkyl groups include cyclohexylethyl, cyclohexylmethyl, 3-cyclopentylpropyl and the like.

The term "$C_2-C_6$ alkenyl" refers to a group containing 2 to 6 carbon atoms and one double bond and the term "$C_3-C_{10}$" alkenyl refers to a group containing 3 to 10 carbon atoms and one double bond. The groups can be branched or straight chain. Examples of such groups include 2-propenyl ($-CH_2-CH=CH_2$), 1-butenyl ($-CH=CHCH_2CH_3$) and the like.

The term "$(C_5-C_8)$cycloalkenyl" represents an olefinically unsaturated ring having five to eight carbon atoms, eg., cyclohexenyl, cyclopentenyl, etc.

The term "$(C_5-C_8)$cycloalkenyl-$(C_1-C_3)$alkyl" represents a linear $C_1-C_3$ group substituted with a $(C_5-C_8)$alkenyl group.

The term "phenyl" includes a benzene ring as well as a benzene ring substituted with one or two $C_1-C_2$ alkyl groups.

The term "phenyl $(C_1-C_3)$ alkyl" represents a linear $C_1-C_3$ alkyl chain substituted at a terminal carbon with a benzene ring. Typical phenylalkyl groups are phenmethyl, phenethyl and phenpropyl.

The term "$(C_1-C_{10})$ alkanoyl" represents group of formula $C(O)(C_1-C_9$ alkyl). Typical $C_1-C_{10}$ alkanoyl groups include acetyl, propanoyl, butanoyl and the like.

The term "amino-blocking group" is used herein as it is frequently used in synthethic organic chemistry, to refer to a group which will prevent an amino group from reacting with the carbonyl group instead of the piperidine nitrogen as shown in Scheme 3 herein, but which can be removed from the amine when it is desired to do so. Such groups are discussed by T. W. Greene in chapter 7 of *Protective Group in Organic Synthesis*, John Wiley and Sons, New York, 1981, and J. W. Barton in chapter 2 of *Protective Groups in Organic Chemistry*, J. F. W. McOmie, ed., Plemun Press, New York, 1973, which are incorporated herein by reference in their entirety. Preferred amino blocking groups include tertiary-butyloxycarbonyl, benzyloxycarbonyl and carbamates such as benzylcarbamate, vinylcarbamate and cinnamylcarbamate.

While all of the compounds of the present invention are useful peripheral opioid antagonists, certain of the present compounds are preferred for that use. Preferably, $R^1$ is hydrogen; $R^2$ is methyl; $R^3$ is phenyl, phenyl-$(C_1-C_3$ alkyl), $(C_3-C_8)$ cycloalkyl, $(C_3-C_8)$ cycloalkyl-$(C_1-C_3)$ alkyl especially cyclohexylmethyl, phenyl, benzyl, or isobutyl; $R^4$ is hydrogen or $(C_3-C_8)$ cycloalkyl, especially cyclohexyl; $R^5$ is $-C(O)(CH_2)_mC(O)R^6$, where $R^6$ is $NH_2$, $-OCH_2CH_3$ or especially $-OH$, and m is 3; and n is 1 or preferably 2.

While all of the intermediates of the present invention are useful for the synthesis of peripherally selective opioid antagonists, certain of the intermediates are preferred for that use. Preferably, $R^1$ is hydrogen; $R^2$ is $(C_1-C_6)$alkyl, most preferably methyl; $R^3$ is $(C_3-C_8)$ cycloalkyl $(C_1-C_3)$alkyl especially cyclohexylmethyl, or isobutyl, $R^4$ is hydrogen or cycloalkyl, especially cyclohexyl; and n is 1 or especially 2.

Other preferred aspects of the present invention are set forth hereinbelow.

The piperidines of the invention as illustrated in Formula I can occur as the trans and cis stereochemical isomers by virtue of the substituents at the 3- and 4-positions. The present invention encompasses the individual trans stereoisomers including individual enantiomers as well as the racemic mixtures. The compounds of the present invention are those isomers in which the $R^2$ group at the 3-position is situated on the opposite side of the ring, i.e. trans, to the methyl group in the 4-position and on the same side of the ring, i.e. Zusammen or Z, relative to the higher priority phenyl group at the 4-position. These trans or Z-isomers exist as the 3R,4R-isomers as shown in Formula III

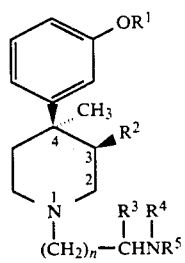

III or the 3S,4S-isomer as represented in Formula IV

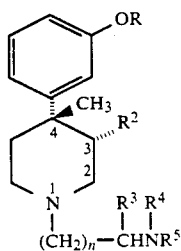

IV

The present invention contemplates both the individual 3R,4R- and 3S,4S-stereoisomers, as well as mixtures of these stereoisomers. The most preferred compounds are those of Formula III in which the configuration is 3R,4R. These compounds have been found to be peripheral opioid antagonists with little or no agonist activity.

Also, when $R^3$ is not hydrogen, the carbon atom attached to $R^3$ is asymmetric. As such, this class of compounds can further exist as the individual R or S stereoisomers, or the racemic mixture of the isomers, and all are contemplated within the scope of the present invention. The preferred stereoisomers are those in which the chiral center to which $R^3$ is bound is S, i.e., those stereoisomers in which the configuration at the three chiral centers is 3R, 4R, S.

Furthermore, when $R^5$ is an arginine residue, ie. $C(O)CH[(CH_2)_3NHC(NH)NHNO_2]NHC(O)W$, or $R^6$ an alphaamino acid residue ie. $NHCHC(O)R^8]R^9$, another asymmetric carbon is introduced into the molecule. As such, these classes of compounds can exist as the individual R or S stereoisomers, or the racemic mixture of the isomers, and all are contemplated within the scope of the present invention.

The terms "R" and "S" are used herein as commonly used in organic chemistry to denote specific configuration of a chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counter-clockwise relationship of group priorities (highest to second lowest) when viewed along the bond toward the lowest priority group. The priority of groups is based upon their atomic number (heaviest isotope first). A partial list of priorities and a discussion of stereo chemistry is contained in the book: *The Vocabulary of Organic Chemistry*, Orchin, et al., John Wiley and Sons Inc., publishers, page 126, which is incorporated herein by reference.

As set forth hereinabove racemic mixtures as well as the substantially pure stereoisomers of the compound of Formula I are contemplated as within the scope of the instant invention. By the term "substantially pure", it is meant that at least about 90 mole percent, more preferably at least about 95 mole percent and most preferably at least 98 mole percent of the desired stereoisomer is present compared to other possible stereoisomers.

Preferred compounds of the instant invention include:

Q—$(CH_2)_2CH(E)NHC(O)(CH_2)_2C(O)OH$;
Q—$(CH_2)_2CH[CH_2CH(CH_3)_2]NHC(O)(CH_2)_2$-$C(O)OCH_2CH_3$; Q—$(CH_2)_2CH[CH_2CH(CH_3)_2]NH$-$C(O)(CH_2)_3C(O)OH$; Q—$(CH_2)_2CH(U)NH$-$C(O)(CH_2)_3C(O)OH$; $Q(CH_2)_2CH(D)NHC(O)CH_3$; $QCH_2CH(K)NHC(O)CH_2C(O)OCH_2CH_3$; $QCH_2CH(K)NHC(O)CH_2C(O)OH$; $QCH_2CH(K)NHC(O)(CH_2)_2C(O)OH$; $QCH_2CH(E)NHC(O)(CH_2)_3C(O)OH$; $Q(CH_2)_2N(U)C$-$(O)(CH_2)_2C(O)O(CH_2)_2CH_3$; $Q(CH_2)_3N(U)C$-$(O)(CH_2)_3C(O)(CH_2)_3C(O)OCH_2CH_3$; $Q(CH_2)_3N(U)C(O)(CH_2)_3C(O)NH_2$; $Q(CH_2)_2N(U)C$-$(O)CH_2C(O)NHCH_2C(O)NHCH_3$; $Q(CH_2)_2N(D)C(O)(CH_2)_2$-$C(O)NHCH[CH_2CH(CH_3)_2]C(O)OH$; $Q(CH_2)_2NHC(O)CH[NH$-$C(O)CH_3](CH_2)_3NHC(NH)NHNO_2$; $Q(CH_2)_2N(U)C$-$(O)(CH_2)_2C(O)OCH_2CH(CH_3)_2$; (3S,4S)—(S-)—T—OH; (−)(3S,4S)—(R)—T—OH; (3R,4R)—(S-)—T—OH; (3R,4R)—(S)—T—OCH_3; (3R,4R)—(S-)—T—OCH_2CH_3; (3R,4R)—(S)—T—O(CH_2)_2CH_3; (3S,4S)—(S)—T—OCH_2CH(CH_3)_2; (3R,4R)—(S-)—T—OCH_2CH(CH_3)_2; (3R,4R)—(S-)—T—O(CH_2)_6CH_3; (3S,4S)—(R-)—T—OCH_2CH(CH_3)_2; (3R,4R)—(R-)—T—OCH_2CH(CH_3)_2; (3S,4S)—(S)—T—OCH_2-$C(O)NH_2$; (3R,4R)—(S)—T—OCH_2C(O)NH_2$; (3S,4S)—(S)—T—OCH_2C(O)NHCH_3$; (3R,4R)—(S-)—T—OCH_2C(O)NHCH_3$; (3S,4S)—(S)—T—OCH_2-$C(O)NHCH_2CH_3$; (3R,4R)—(S)—T—OCH_2-$C(O)NHCH_2CH_3$; (3S,4S)—(S)—T—O—G; and (3R,4R)—(S)—T—O—J.

wherein:

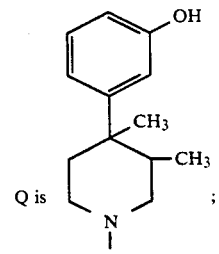

Q is

E is —$CH_2$— 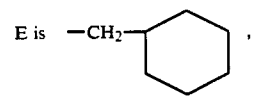,

U is 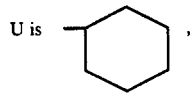,

D is 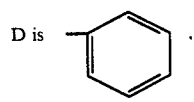.

K is 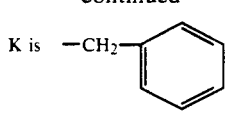

T is 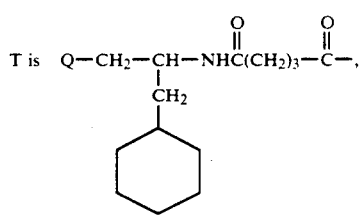

G is 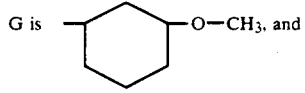

J is 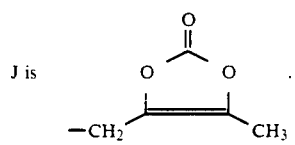

The piperidines of this invention form pharmaceutically acceptable acid addition salts with a wide variety of inorganic and organic acids. Typical acids generally used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. Such pharmaceutically acceptable salts are within the scope of the present invention.

The compounds of the present invention can be prepared by a variety of procedures well known to those skilled in the art. The 3-substituted-4-methyl-4-(3-hydroxy- or alkanoyloxyphenyl)piperidine derivatives employed as starting materials in the synthesis of the instant compounds can be prepared by the general procedure taught by Zimmerman in U.S. Pat. No. 4,115,400 (1978), incorporated herein by reference. The starting material for the synthesis of the preferred compounds of the present invention, (3R,4R)-4-(3-hydroxyphenyl)-3,4-dimethylpiperidine, can be prepared by the procedure of Barnett in U.S. Pat. 4,581,456, herein incorporated by reference, but adjusted as described in such patent so that the β-stereochemistry is primarily obtained. This process is depicted in Scheme 1, wherein $R^{20}$ is $C_1$-$C_3$ alkoxy, $R^{21}$ is $C_1$-$C_6$ alkyl, $R^{22}$ is $C_1$-$C_4$ alkyl, $R^{23}$ and $R^{24}$ independently are $C_1$-$C_3$ alkyl or, when taken together with the nitrogen atom to which they are attached, form piperidine, piperazine, N-methylpiperazine, morpholine or pyrrolidine, and Y is a leaving group such as halogen.

Scheme 1

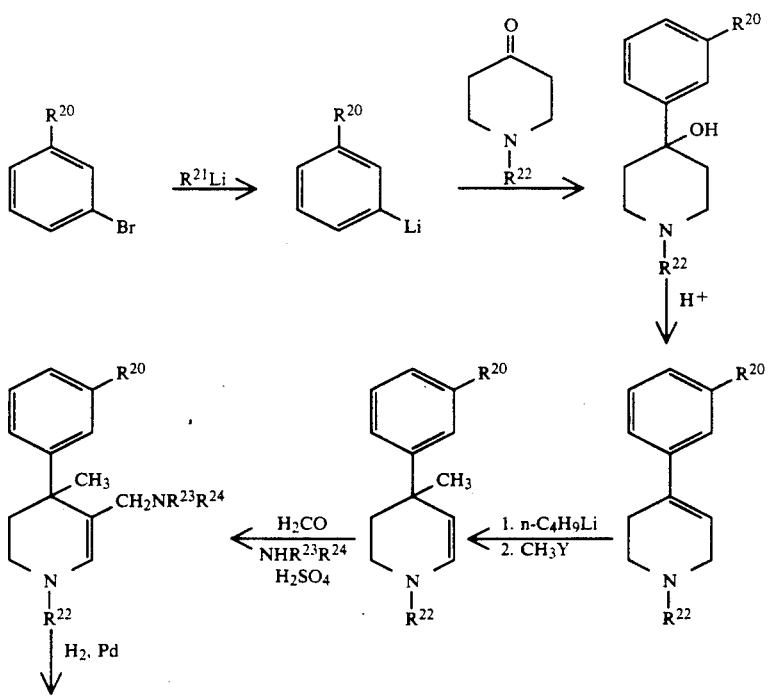

Scheme 1

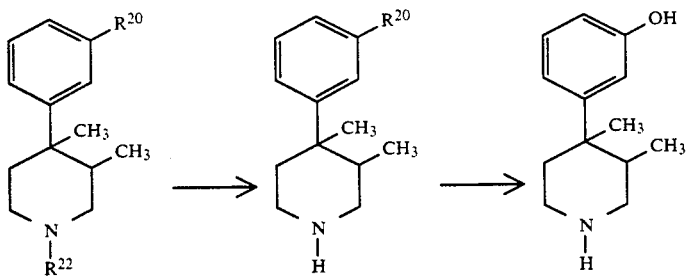

-continued

The first step of the above-described process involves the formation of the 3-alkoxyphenyllithium reagent by reacting 3-alkoxybromobenzene with an alkyllithium reagent. This reaction is typically performed under inert conditions and in the presence of a suitable non-reactive solvent such as dry diethyl ether or preferably dry tetrahydrofuran. Preferred alkyllithium reagents used in this process are n-butyllithium, and especially sec.-butyllithium. Generally, approximately an equimolar to slight excess of alkyllithium reagent is added to the reaction mixture. The reaction is conducted at a temperature between about −20° C. and about −100° C., more preferably from about −50° C. to about −55° C.

Once the 3-alkoxyphenyllithium reagent has formed, approximately an equimolar quantity of a 1-alkyl-4-piperidone is added to the mixture while maintaining the temperature between −20° C. and −100° C. The reaction is typically complete after about 1 to 24 hours. At this point, the reaction mixture is allowed to gradually warm to room temperature. The product is isolated by the addition to the reaction mixture of a saturated sodium chloride solution in order to quench any residual lithium reagent. The organic layer is separated and further purified if desired to provide the appropriate 1-alkyl-4-(3-alkoxyphenyl)piperidinol derivative.

The dehydration of the 4-phenylpiperidinol prepared above is accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid in toluene or benzene. This reaction is typically conducted under reflux conditions, more generally from about 50° C. to about 150° C. The product thus formed is generally isolated by basifying an acidic aqueous solution of the salt form of the product and extracting the aqueous solution with any one of several water immiscible solvents. The resulting residue following evaporation may then be further purified if desired.

The 1-alkyl-4-methyl-4-(3-alkoxyphenyl)tetrahydropyridine derivatives are prepared by a metalloenamine alkylation. This reaction is preferably conducted with n-butyllithium in tetrahydrofuran under an inert atmosphere, such as nitrogen or argon. Generally, a slight excess of n-butyllithium is added to a stirring solution of the 1-alkyl-4-(3-alkoxyphenyl)-tetrahydropyridine in THF cooled to a temperature in the range of from about −50° C. to about 0° C., more preferably from about −20° C. to about −10° C. This mixture is stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water is added to the reaction mixture and the organic phase is collected. The product may be purified according to standard procedures, but it is desirable to purify the crude product by either distilling it under vacuum or slurrying it in a mixture of hexane:ethyl acetate (65:35, v:v) and silica gel for about two hours. According to the latter procedure, the product is then isolated by filtration and evaporating the filtrate under reduced pressure.

The next step in the process involves the application of the Mannich reaction of aminomethylation to non-conjugated, endocyclic enamines. This reaction is carried out by combining from about 1.2 to 2.0 equivalents of aqueous formaldehyde and about 1.3 to 2.0 equivalents of the secondary amine $NHR^{23}R^{24}$ in a suitable solvent. While water is the preferred solvent, other non-nucleophilic solvents such as acetone and acetonitrile may also be employed in this reaction. The pH of this solution is adjusted to approximately 3.0–4.0 with an acid which provides a non-nucleophilic anion. Examples of such acids include sulfuric acid, the sulfonic acids such as methanesulfonic acid and p-toluenesulfonic acid, phosphoric acid, and tetrafluoroboric acid. The preferred acid is sulfuric acid. To this solution is added one equivalent of a 1-alkyl-4-methyl-4-(3-alkoxyphenyl)tetrahydropyridine, typically dissolved in aqueous sulfuric acid, and the pH of the solution readjusted to from 3.0–3.5 with the non-nucleophilic acid or a secondary amine as defined above. While maintenance of this pH during the reaction is preferred for optimum results, this reaction may be conducted at a pH in the range of from about 1.0 to 5.0. The reaction is substantially complete after about 1 to 4 hours, more typically about 2 hours, when conducted at a temperature in the range of from about 50° C. to about 80° C., more preferably at about 70° C. The reaction is next cooled to approximately 30° C. and added to a sodium hydroxide solution. This solution is extracted with a water immiscible organic solvent, such as hexane or ethyl acetate, and the organic phase, following thorough washing with water to remove any residual formaldehyde, is evaporated to dryness under reduced pressure.

The next step of the process involves the catalytic hydrogenation of the 1-alkyl-4-methyl-4-(3-alkoxyphenyl)-3-tetrahydropyridinemethanamine prepared above to the corresponding trans 1-alkyl-3,4-dimethyl-4-(3-alkoxyphenyl)piperidine. This reaction actually occurs in two steps. The first step is the hydrogenolysis reaction wherein the exo C-N bond is reductively cleaved thereby generating the 3-methyltetrahydropyridine. In the second step, the 2,3-double bond in the tetrahydropyridine ring is reduced thereby affording the desired piperidine ring.

Reduction of the enamine double bond introduces the crucial relative stereochemistry at the 3 and 4 carbon atoms of the piperidine ring. The reduction does not occur with complete stereoselectivity. The catalysts employed in the process are chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome has been shown to be dependent on the quantity of catalyst employed. The quantity of catalyst required to produce the desired stereochemical result has been reported to be dependent upon the purity of the starting materials in regard to the presence or absence of various catalyst poisons. Typically 2.5 equivalents of catalyst are used. If hydrogen uptake is not complete, more catalyst is added.

The hydrogen pressure in the reaction vessel is not critical but can be in the range of from about 5 to 200 psi. Concentration of the starting material by volume should preferably be around 20 ml. of liquid per gram of starting material, although an increased or decreased concentration of the starting material can also be employed. Under the conditions specified herein, the length of time for the catalytic hydrogenation is not critical because of the inability for over-reduction of the molecule. While the reaction can continue for up to 24 hours or longer, it is not necessary to continue the reduction conditions after the uptake of the theoretical two moles of hydrogen. The product is isolated by filtering the reaction mixture through infusorial earth and evaporating the filtrate to dryness under reduced pressure. Further purification of the product thus isolated is not necessary and preferably the diastereomeric mixture is carried directly on to the following reaction.

The alkyl substituent is next removed from the 1-position of the piperidine ring by standard dealkylation procedures. Preferably, a chloroformate derivative, especially the vinyl or phenyl derivatives, are employed and removed with acid. Next, the alkoxy compound prepared above is demethylated to the corresponding phenol. This reaction is generally carried out by reacting the compound in a 48% aqueous hydrobromic acid solution. This reaction is substantially complete after about 30 minutes to 24 hours when conducted at a temperature between 50° C. to about 150° C., more preferably at the reflux temperature of the reaction mixture. The mixture is then worked up by cooling the solution, followed by neutralization with base to an approximate pH of 9.8. This aqueous solution is extracted with a water immiscible organic solvent. The residue following evaporation of the organic phase is then preferably used directly in the following step.

The compounds employed as starting materials to the compounds of the invention can also be prepared by brominating the 1-alkyl-4-methyl-4-(3-alkoxyphenyl)-3-tetrahydropyridinemethanamine prepared above at the 3-position, lithiating the bromo intermediate thus prepared, and reacting the lithiated intermediate with the halide $CH_3Y$ to provide the corresponding 1-alkyl-3,4-dimethyl-4-(3-alkoxyphenyl)tetrahydropyridinemethanamine. This compound is then reduced and converted to the starting material as indicated above.

As noted above, the compounds of the present invention can exist as the resolved stereoisomers. The preferred procedure employed to prepare the resolved starting materials used in the synthesis of these compounds includes treating a racemic mixture of a 1-alkyl-3,4-dimethyl-4-(3-alkoxyphenyl)piperidine with either (+)- or (−)-di-benzoyl tartaric acid to provide the resolved intermediate. This compound is dealkylated at the 1-position with vinyl chloroformate and finally converted to the desired 4-(3-hydroxyphenyl)piperidine isomer. This reaction is set forth in the following Scheme 2 wherein $R^{20}$ and $R^{22}$ are as defined above:

Scheme 2

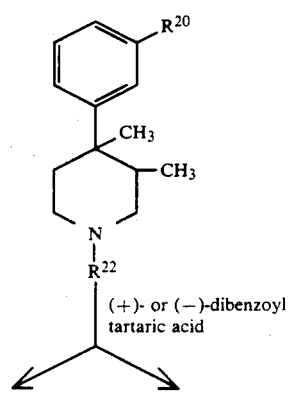

Scheme 2

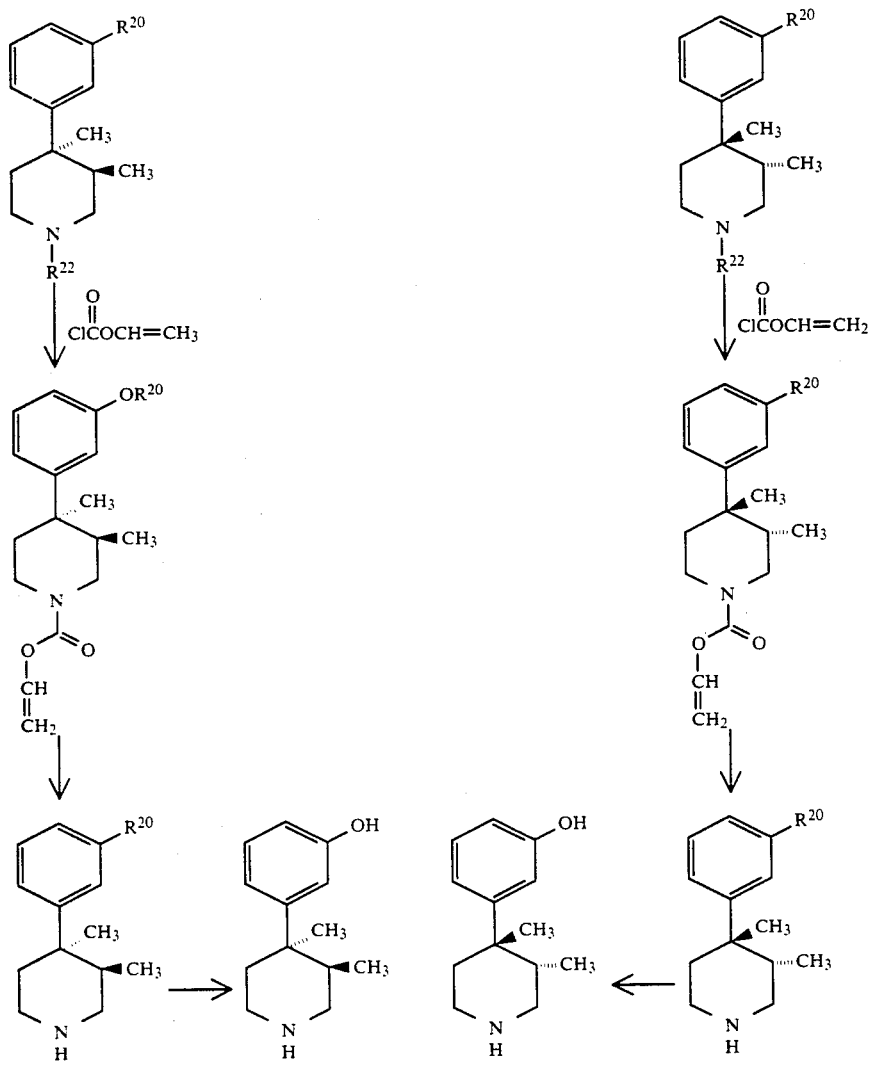

The 3,4-dimethyl-4-(3-hydroxyphenyl)piperidine prepared as shown in Scheme 2 can then be reacted with an appropriate acylating agent to provide the intermediate amide of the instant invention, Formula IIb, which is then reduced under standard conditions to give the intermediate of Formula IIa of the present invention. This reaction can be represented by the following Scheme 3 wherein $R^3$, $R^4$, and n are as defined above and Z is hydrogen when $R^4$ is phenyl or an amino blocking group when $R^4$ is other than phenyl:

Scheme 3

-continued
Scheme 3

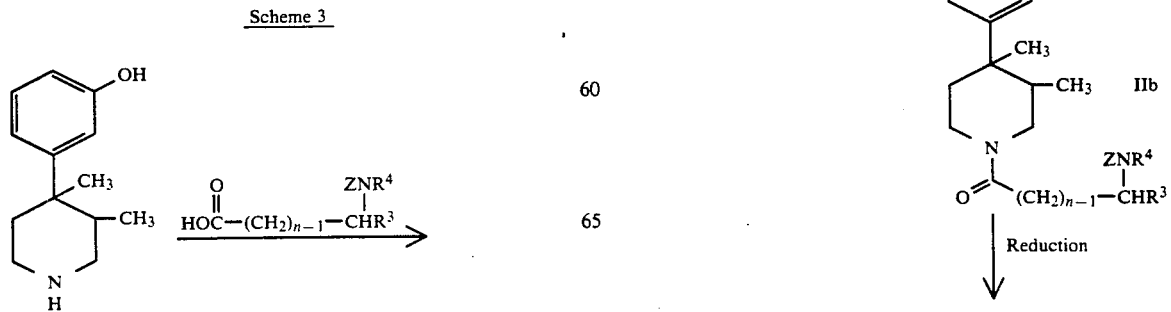

-continued
Scheme 3

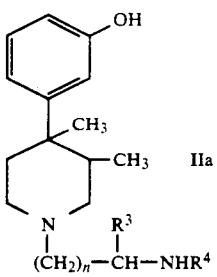

When R[4] is not phenyl, it is necessary to protect the nitrogen of the amino acid prior to reaction with the starting 3,4-dimethyl-4-(3-hydroxyphenyl)piperidine. Standard nitrogen protecting groups, (amino blocking group) are acceptable but preferred amino blocking groups include the tertiary-butyloxycarbonyl (t—BOC) group, benzyloxycarbonyl (C$_6$H$_5$CH$_2$O(O)—), benzylcarbamate, vinylcarbamate and cinnanylcarbamate.

This protection step with for example the t-BOC group is conveniently performed by dissolving the unprotected amino acid in a mixture of water and an unreactive, water miscible solvent, such as tetrahydrofuran or preferably dioxane, in a ratio of approximately 1:2 respectively. To this solution is then added between 1.5 and 2.0 equivalents of an aqueous base, typically sodium hydroxide, at ice bath temperatures, typically from 0° to 10° C. To this solution is then added approximately 2.0 equivalents of di-tert-butyl dicarbonate. The reaction is complete in about 1 to 2 hours at a temperature ranging from 0° C. to ambient. The next step is careful acidification of the reaction mixture to a pH of approximately 2. Acidification is accomplished by the addition of a minerial acid, typically hydrochloric, hydrobromic, sulfuric or especially sodium hydrogen sulfate. The desired product is then extracted from the reaction mixture in an inert, water immiscible solvent and isolated by crystallization. The product thus formed can be further purified, if needed, by any of several routine methods, including recrystallization, chromatography and related techniques.

In the next step in the process of Scheme 3, coupling reagent commonly used in the synthesis of peptides can be employed. Examples of such coupling reagents include the carbodimides such as N,N'-di-cyclohexylcarbodiimide, N,N'-diisopropylcarbodiimide, or N,N'-diethylcarbodimide; the imidazoles such as carbonyldiimidazole; as well as reagents such as N-ethoxycarbonyl-2-ethoxy-1,2-dihydroquinoline (EEDQ). The direct coupling of a substituted carboxylic acid and 3,4-dimethyl-4-(3-hydroxyphenyl)piperidine is conveniently carried out by adding about an equimolar quantity or slight excess of the coupling reagent to a solution of the substituted carboxylic acid, with equimolar quantitites of 3,4-dimethyl-4-(3-hydroxyphenyl)-piperdine and 1-hydroxybenzotriazole. The reaction is carried out in an inert organic solvent such as dichloromethane or N,N-dimethylformamide, and the reaction is complete within about twenty four to seventy two hours at a temperature of about 0° C. to about 30° C. The product is then typically isolated by crystallization and filtration. The product thus formed can be further purified, if needed, by any of several routine methods, including recrystallization from common solvents, chromatography and related purification techniques.

These coupled compounds can now be reduced to provide the intermediates of the present invention. Typical reducing agents suitable for use include the hydride reducing agents such as lithium aluminum hydride and sodium bis(2-methoxyethoxy) aluminum hydride (Red A1), which is preferred. An excess of reducing agent is combined with the coupled intermediate in a mutual solvent, typically toluene. The reaction is substantially complete after about one to about eighteen hours when conducted at a temperature in the range of about ° C. to about 100° C.

Some of the intermediates (Formula IIa) of the present invention can alternately be prepared by direct alkylation of 3,4-dimethyl-4-(3-hydroxyphenyl) piperidine with a haloalkylnitrile followed by reduction of the nitrile to give a primary amine. The amine can optionally be reductively alkylated to give other intermediates contemplated by this invention. This reaction is represented by the following Scheme 4 wherein R[4] and n are defined above and X is chloro, bromo or iodo:

Scheme 4

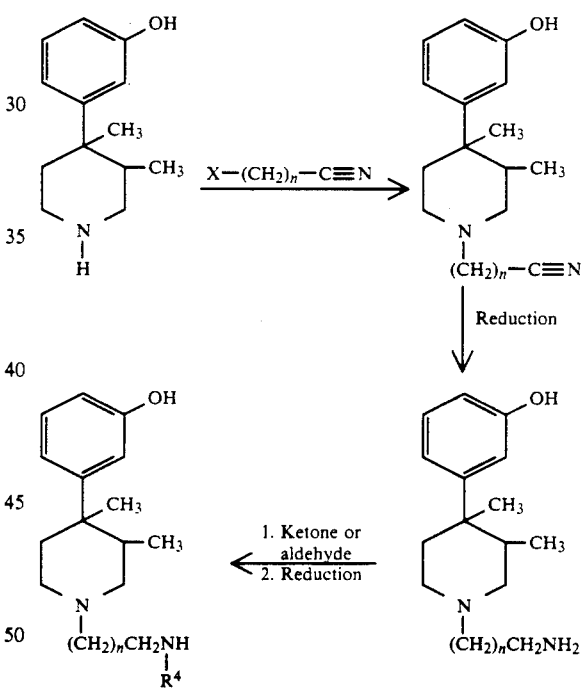

The reaction is conducted by combining approximately equimolar amounts of the two starting materials in a mutual solvent. A slight excess of the haloalkylnitrile can be used to assure complete reaction. Typical inert solvents for use in this reaction include aprotic solvents such as N,N-dimethylformamide and the like. The reaction is conducted in the presence of a base, such as sodium bicarbonate or potassium carbonate, which acts to neutralize the hydrohalic acid formed as a side product of the reaction. The reaction is generally complete after about 30 minutes to 24 hours at a temperature from about 40° C. to about 100° C. The nitrile is isolated under standard conditions. This product is then subjected to the hydride reducing conditions previously discussed. Alternatively, the nitrile can be subjected to standard catalytic hydrogenation over Raney nickel or a noble metal catalyst, such as palladium or platinum, preferably in an acidic solvent such as acetic acid. The product is isolated under standard conditions.

The amine thus formed can now be functionalized under standard reductive alkylation procedures. The reaction proceeds by adding a slight excess of an appropriate aldehyde or ketone, especially a cycloalkanone such as cyclohexanone or cyclopentanone, to a solution of the above-synthesized amine and a base such as potassium hydroxide in a lower alkanol such as ethanol or especially methanol. This solution is stirred at room temperature for from 30 minutes to 18 hours. At this time an equimolar to slight excess of a solution of a boronhydride reducing agent, especially sodium cyanoborohydride, in the same lower alkanol is added and the reaction mixture is stirred at room temperature for an additional 30 minutes to 18 hours. The reaction is now treated with a strong base such as potassium hydroxide, to decompose any boron-nitrogen complexes present and the product is isolated under standard conditions. The product can be purified as desired by chromatography, crystallization or related techniques.

The compounds of the present invention can be conveniently prepared by contacting the particular amine intermediate prepared as described hereinabove in a typical amide forming reaction. For example, the amine can be reacted with the desired carboxylic acid compound using a coupling agent as described hereinabove. Alternatively, an acid anhydride can be used if available. Examples of these procedures are described hereinbelow.

The following examples and preparations are provided for the purpose of illustration and are not to be construed as limiting the instant invention.

As used in the instant examples the following terms have the meanings indicated. "Hobt" refers to 1-hydroxybenzotriazole hydrate. "THF" refers to tetrahydrofuran. "DMF" refers to dimethylformamide. "TEA" refers to triethylamine. "DCC" refers to dicyclohexylcarbodiimide. "di-t-BOC" refers to di-tert-butyl dicarbonate (O[CO$_2$C)CH$_3$)$_3$]) and "tBOC" refers to —CO$_2$C(CH$_3$)$_3$. "Red Al" refers to sodium bis(2-methoxyethoxy) aluminum hydride. "Q-H" refers to trans-dimethyl-4-(3-hydroxyphenyl)piperidine, i.e., where Q is

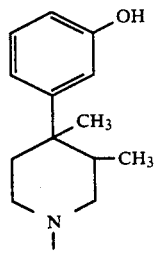

The column chromatography procedure used involved gravitational flow with Allied Fischer silica gel (70-150 mesh). Gradient solvent procedures were employed using the solvent systems specified in the particular example. The gradient procedure involved starting the indicated solvent system and incrementally changing the solvent mixture until the indicated final solvent system was obtained. Fractions containing product were evaporated generally under reduced vacuum to provide product.

Preparative liquid chromatography was performed with the Waters Prep LC/500 apparatus using dual silica prep pack cartridges. Gradient solvent systems were employed as listed in the particular example.

For those examples indicated, purification of the specified compound was accomplished by preparative, centrifugal, thin layer chromatography on a Harrison Model 7924A Chromatron using Analtech silica gel GF rotors. The plate thickness and solvent system employed are indicated in the particular example Optical rotations were obtained using methanol as the solvent.

The hydrochloride salt of the particular compound was prepared by placing the free base into ethyl ether. While stirring this ether solution, a solution of HCl in ethyl ether was added dropwise until the solution became acidic. A precipitate formed which was filtered and dried to provide the corresponding hydrochloride salt of the free base.

Preparation I

Synthesis of (+)-(3R,4R)-dimethyl-4-(3-hydroxyphenyl)-piperidine (hereinafter "(3R,4R)-QH").

3-Bromophenol was combined with an equal molar amount of 2-bromopropane in ethanol and in the presence of potassium carbonate to provide 3-bromoisopropoxybenzene.

The 3-bromo-i-propoxybenzene (200 g, 0.08703 mol) was combined with THF (540 ml) under nitrogen and cooled to about −75° C. n-Butyl lithium (565 ml, 0.8306 mol) was added dropwise while maintaining the mixture at less than −70° C. After 2 hours 1,3-Dimethyl-4-piperidone (106.7 g, 0.8389 mol) was added while maintaining the temperature of the mixture between −80° C. and −70° C. After stirring 2 hours at −70° C., the reaction mixture was then added to 6N HCl (280 ml) while maintaining the temperature at 20°-25° C. The pH was adjusted to 1 with 12 N HCl. The aqueous layer containing product was separated and heptane (320 ml) was added along with 50% NaOH (48 ml, pH=13−14) and the resulting mixture allowed to stand overnight. The mixture was heated to 45°-50° C. and the upper layer was separated. The remaining aqueous layer was extracted with heptane (320 ml) at 45°-50° C. The combined organic fractions were washed with de-ionized water (120 ml) at 45°-50° C. The resulting organic layer was vacuum distilled at a pot temperature of about 55° C. at 100 mmHg. Crystallization from heptane and drying provided 151.8 g of 3-(3-i-propoxyphenyl)-1,3-dimethyl-4-hydroxypiperidine. Melting point 75.0°-76.0° C.

This 4-hydroxypiperidine (463 g, 1.758 mol) was combined with ethyl acetate (2275 ml) under nitrogen. The solution was cooled to 0°-5° C. and ethyl chloroformate (205 ml, 2.144 mol) was added while maintaining the temperature below 15° C. The reaction mixture was stirred for an additional 3 hours at room temperature. The mixture was then added to 5N NaOH (750 ml) with stirring (pH=12−13) the organic layer was separated and washed with de-ionized water. Solvate was removed by evaporation at 50° C. to provide 591 g of a viscous oil.

This viscous oil (284.8 g) was dissolved in ethanol (2.6 L) and warmed to 55° C. under nitrogen. (+)-Di-p-toluoyl-D-tartaric acid, monohydrate was added and the solution heated to reflux. After stirring overnight at room temperature, the mixture was cooled to 0°-5° C. before filtering. The filter cake was washed with cold ethanol, air dried for 30 minutes and then vacuum dried at 45°-50° C. Recrystallization from ethanol provided 201.7 g of product with a melting point of 153.5°-155° C. (dec). This material had a ratio of isomers by proton NMR of 97:3.

Product prepared in this manner (411.7 g) was added to heptane (1200 ml) and 2N NaOH (550 ml) over a 15 minute period. pH of the mixture was adjusted to about 13 with 50% NaOH and stirred until all solid had dissolved. The layers were separated and the organic layer washed with 1N NaOH (275 ml), de-ionized water (275 ml) and then saturated aqueous sodium chloride (210 ml). The organic fraction was dried over 175 g of sodium sulfate, filtered and washed with heptane (125 ml). The solvate was removed by evaporation to provide 189.4 g of a colorless viscous oil. $[\alpha]_{589}$ of $-6.92°$ (c=1.01 methanol).

This product (50.0 g) and decalin (250 ml) were heated at 190°-195° C. for 19 hr. under nitrogen while removing the ethanol formed by distillation. The solution was cooled to 15°-20° C. under nitrogen and 1N HCl (155 ml) was added with stirring. The aqueous fraction was separated and extracted with heptane (2×30 ml). The pH of the aqueous layer was adjusted to about 13 by adding 50% NaOH and extracted with heptane 36.5 g of a yellow-orange liquid were removed from the organic layer. $[\alpha]_{589} = -67.24°$.

This product (19.6 g) was combined with THF (175 ml) and cooled to $-15°$ C. to $-20°$ C. under nitrogen. n-Butyl lithium (70.0 ml) was added with stirring over about 0.5 hour while maintaining the internal temperature at about $-10°$ C. to about $-20°$ C. The mixture was stirred for another 0.5 hour at $-10°$ C. to $-15°$ C. and then cooled to $-45$ to $-50°$ C. Dimethyl sulfate (7.7 ml) was added slowly over 20-30 minutes while maintaining the temperature between $-45°$ C. and $-50°$ C. The mixture was then stirred for an additional 30 minutes at about $-50°$ C. This reaction mixture was then added slowly to a dilute solution of aqueous ammonium hydroxide (15.5 ml aqueous ammonium hydroxide solution plus 55 ml de-ionized water) at 0°-5° C. The mixture was warmed to 20°-25° C. over 30-45 minutes and stirred an additional 2 hours at 20°-25° C. The organic layer was recovered and washed with de-ionized water followed by removal of solvate by evaporation to provide 21.44 g of 4-(3-i-propoxyphenyl)-1,4,5-trimethyl-2,3-dehydropiperidine as an orange liquid.

The dehydropiperidine (21.2 g) and methanol (195 ml) were combined under nitrogen and cooled to 0°-5° C. Sodium borohydride (4.2 g) was added slowly while maintaining the temperature below 15° C. The reaction mixture was stirred at room temperature Acetone (21 ml) was added to the reaction mixture and stirred for 5 minutes. A saturated solution of sodium bicarbonate (25 ml) was added and the mixture stirred for 5 minutes. The alcohols were removed by evaporation at 50° C. De-ionized water (95 ml) and ethyl acetate (95 ml) were added and the resulting mixture stirred to form a solution. Phases were separated and the organic phase extracted with ethyl acetate (20 ml). Combined organic fractions were washed with de-ionized water (95 ml) and the solvate removed by evaporation at 50° C. to provide (+)-4-(3-i-propoxyphenyl)-1,3,4-trimethyl-piperidine as a yellow liquid (20.5 g).

Dried ethanol (75 ml) and (+)-di-p-toluoyl-D-tartaric acid, monohydrate (12.48 g) were combined and heated to 55°-60° C. under nitrogen. An ethanol solution of the trimethyl piperidine (8.07 g and 20 ml) was added while heating to reflux (about 75° C.). De-ionized water (6 ml) was added to obtain a clear homogeneous solution which was stirred at reflux for 0.5 hour. Cooling, filtering, washing with cold dried ethanol, and drying provided 6.6 g of (+)-4-(3-i-pripoxyphenyl)-1,3,4-trimethylpiperidine/(+)-di-p-toluoyl-D-tartaric acid salt with a melting point 150°-151.5° C. (dec).

Toluene (1400 ml) and 2N NaOH (700 ml) were combined and cooled to 15°-20° C. The piperidine-tartaric salt (395.0 grams) was added with stirring at 15°-25° C. and stirred until all solids had dissolved. The layers were separated and the organic fraction washed with 1N NaOH (385 ml) and di-ionized water (385 ml). The organic fraction was filtered and the solvate removed by evaporation (50° C.) to provide 164.8 g of the free base as an oil. $[\alpha]_{589} = +74.18°$.

To a mixture of the free base (+)-4-(3-i-propoxyphenyl)-1,3,4-trimethyl-piperidine (25 g) and toluene (160 ml) at 80°-90° C. was added phenylchloroformate (17.2 g). The mixture was heated at reflux (110° C.) for 2 hours and then cooled to 45°-50° C. NaOH (5 ml, 50%, in 40 ml water) was added and the mixture stirred with cooling to room temperature. After 30 minutes the layers were separated and the organic layer extracted with a 1:1 mixture of methanol and 1N HCl, a 1:1 mixture of methanol and 1N NaOH, and then extraction by water. Evaporation of the solvate provided 33.9 g of the phenyl piperidineformate as an oil.

The phenyl piperidineformate (13.95 g), 48% HBr (17.4 ml) and glacial acetic acid (4.7 ml) were combined and refluxed for 18 hours. The solution was cooled to room temperature; water (50 ml) was added; and the solution was extracted 3 times with t-butyl methyl ether (30 ml aliquots). The pH of the aqueous phase was adjusted to 8.5-8.8 with 50% NaOH solution. Methanol (15 ml) was added and the pH adjusted to 10.5 with the 50% NaOH solution. The mixture was stirred for 1.5 hours, cooled to 5° C. and filtered to provide the white solid (+)-trans-4-(3-hydroxyphenyl)-3,4-dimethyl-piperidine (7.24 g). $[\alpha]_{365} = +380.37$ (methanol).

Preparation II

Synthesis of trans-3-[4-(3-hydroxyphenyl)-3,4-dimethyl-1-piperidinyl]-1-phenylpropylanine [Q-(CH$_2$)$_2$-CH(C$_6$H$_5$)-NH$_2$].

To a solution of 5.0 gm (30.3 mMol) of DL-3-amino-3-phenylpropionic acid in a mixture of dioxane (100 ml) and water (50 ml) were added 1N aqueous sodium hydroxide (51.7 ml) with stirring and cooling in an ice bath followed by the addition of 12.67 gm (56.9 mMol) of di-tBOC. The reaction mixture was stirred for 1 hour at 0° C. and then for an additional hour at room temperature. The volatiles were partially evaporated at reduced pressure. The remaining aqueous residue was extracted once with ethyl acetate, acidified to pH 2 with saturated aqueous potassium hydrogen sulfate and extracted three times with ethyl acetate. The combined organic extracts were washed with saturated aqueous sodium chloride, dried over magnesium sulfate and concentrated under reduced pressure. The crude product recovered was recrystallized from ethyl acetate/petroleum ether to give 6.3 gm (78.5%) of N-tBOC-3-phenyl-3-aminopropanoic acid as a crystalline solid.

Calculated for $C_{14}H_{19}NO_4$: Theory: C, 63.38; H, 7.22; N, 5.28 Found: C, 63.43; H, 7.42; N, 5.06

To a solution of 1.0 gm (4.9 mMol) of trans-4-(3-hydroxyphenyl)-3,4-dimethylpiperidine in dimethylformamide (50 ml) were added sequentially 1.3 gm (4.9 mMol) N-tBOC-3-phenyl-3-aminopropionic acid, 0.662 gm (4.9 mMol) 1-hydroxybenzotriazole and 1.011 gm (4.9 mMol) dicyclohexylcarbodiimide. The reaction mixture was allowed to stir for 24 hours at room temperature. The reaction mixture was then cooled to 0° C., filtered and the filter cake washed with cold dimethylformamide. The filtrate was concentrated under reduced pressure and the residue dissolved in diethyl ether. The organic solution was washed with cold 1N hydrochloric acid, dried over potassium carbonate and concentrated under reduced pressure to give 1.9 gm (85.8%) trans-1-(N-tBOC-3-phenyl-3-aminopropionyl)-4-(3-hydroxyphenyl)-3,4-dimethylpiperidine.

ms (fd)=452 M+

Calculated for $C_{27}H_{36}N_2O_4$: Theory: C, 71.65 H, B.02; N, 6.19 Found: C, 71.90 H, 7.98N, 6.31

To a solution of 1.9 qm (4 mMol) trans-1-(N-tBOC-3-phenyl-3-aminopropionyl)-4-(3-hydroxyphenyl)-3,4-dimethylpiperidine in dichloromethane (20 ml) and anisole (5 ml) at 0° C. was added trifluoroacetic acid (10 ml) and the solution stirred at 0° C. for 30 minutes and then at ambient temperature for an additional 30 minutes. The reaction mixture was then concentrated under reduced pressure and the residue triturated with ether and filtered. The resulting solid was dissolved in water and the solution was treated with 1N sodium hydroxide to adjust pH to 9.8. This mixture was then extracted with ethyl acetate. The organic extracts were combined, dried over potassium carbonate and concentrated under reduced pressure to give 0.722 gm (51%) crude trans-1-(3-phenyl-3-aminopropionyl)-4 TM (3-hydroxyphenyl)-3,4-dimethylpiperidine.

A solution of 0.700 gm (2 mMol) crude trans-1-(3-phenyl-3-aminopropionyl)-4-(3-hydroxyphenyl)-3,4-dimethylpiperidine in toluene (20 ml) was added to a solution RedAl (7 ml) in toluene (40 ml) and the solution was stirred at 60° C. for 1 hour. The reaction mixture was then poured into ice water buffered at pH 10 and the pH adjusted to 9.8 with 1N hydrochloric acid. The aqueous mixture was then extracted two times with 3:1 n-butanol:toluene. The organic extracts were then combined, dried over potassium carbonate and concentrated under reduced pressure. The crude material was purified by flash silica gel chromatography, eluting with methanol. The fractions containing product were combined, concentrated under reduced pressure and the residue was triturated with hexane to give 0.33 gm (50%) of the title compound as a white solid.

m.p.=50°-70° C.

Calculated for $C_{22}H_{31}N_2O$: Theory: C, 77.83; H, 9.20; N, 8.25; Found: C, 77.73, H, 8.97; N, 7.96.

Preparation III

Synthesis of trans-3-(4-(3-hydroxyphenyl)-3,4-dimethyl-1-piperidinyl)-1-cyclohexylpropylamine. [Q-$(CH_2)_2CH-(C_6H_{11})NH_2$].

To a solution of 25 gm (152 mMol) DL-3-amino-3-phenylpropionic acid in acetic acid (270 ml) were added platinum oxide (5 gm) and the mixture was pressurized to 60 p.s.i. with hydrogen and then stirred at 40° C. for 1 hour. The reaction mixture was cooled to room temperature and filtered. The filtrate was then concentrated under reduced pressure and the resulting residue diluted with sufficient 6N hydrochloric acid to effect solvation. After stirring for 1 hour at room temperature a precipitate began to form and the mixture was cooled to 0° C. for 18 hours. DL-3-amino-3-cyclohexylpropionic acid hydrochloride was recovered by filtration. A yield of 21.0 gm (64%) was realized after drying filtered solid in an oven under vacuum.

m.p.=230°-232° C.

ms (fd)=172 (M++1), 127 (M-43($CO_2$))

Calculated for $C_9H_{18}NO_2Cl$: Theory: C, 52.05; H, 8.74; N, 6.74 Found: C, 52.00; H, 8.52; N, 6.56

The title compound was prepared by subjecting DL-3-amino-3-cyclohexylpropionic acid hydrochloride (21.48 gm) to the sequence of reactions performed on DL-3-amino-3-phenylpropionic acid as described in Preparation II and 0.740 gm of product was recovered as a colorless solid.

ms (fd)=345 (M+)

Preparation IV

Synthesis of trans-1-(4-(3-hydroxyphenyl)-3,4-dimethyl-1-piperidinyl)-3-amino-5-methylhexane. [Q—$(CH_2)_2CH(NH_2)-CH_2CH(CH_3)_2$].

To a solution of 43.06 gm (500 mMol) isovaleraldehyde in ethanol (150 ml) were added 52 gm (500 mMol) malonic acid followed by 57.75 gm (750 mMol) ammonium acetate. The suspension was stirred at reflux for 5 hours and the resulting solution was then cooled to 0° C. The resulting solid was filtered, washed with 1:1 ethyl acetate:ethanol (200 ml) and dried under vacuum for 18 hours to give 40 gm of crude 3-amino-5-methylhexanoic acid.

ms (fd)=145 (M+)

The title compound was prepared by subjecting DL-3-amino-5-methylhexanoic acid (16.1 gm, 111 mMol) to the sequence of reactions performed on DL-3-amino-3-phenylpropionic acid as described in Preparation II to provide 2.41 gm of product.

m.p.=50°-55° C.

ms (fd)=318 (M+)

Calculated for $C_{20}H_{34}N_2O$: Theory: C, 75.42; H, 10.76; N, 8.80 Found: C, 75.64; H, 10.97; N, 8.65

Preparation V

Synthesis of (−)-1,5-dioxo-5-[(phenylmethyl)amino]-pentylamino-5-[[imino(nitroamino)methyl]amino]-pentanoic acid. [($C_6H_5$)$CH_2NHC(O)(CH_2)_3$-$C(O)NHCH(CO_2H)-(CH_2)_3NHC(N)NHNO_2$].

To a solution of 25 gm (220 mMol) glutaric anhydride in dichloromethane (250 ml) was added a solution of 26.4 ml (242 mMol) benzylamine in dichloromethane (50 ml) dropwise. The reaction mixture was stirred for 3 hours at room temperature. The reaction mixture was then poured into diethyl ether (500 ml) and the resulting solid was filtered. The filter cake was washed with diethyl ether, dried under vacuum and then recrystallized from ethyl acetate to give 24.8 gm (51%) 5-oxo-5-(phenylmethylamino)pentanoic acid as a crystalline solid.

m.p.=83°-84° C.

Calculated for $C_{12}H_{13}NO_2$: Theory: C, 65.14; H, 6.83; N, 6.33 Found: C, 65.38; H, 7.09; N, 6.27

To a solution of 2.0 gm (8.44 mMol) N-w-methyl ester-nitro-L-arginine hydrochloride and 1.64 gm (7.42 mMol) 5-oxo-5-(phenylmethylamino)pentanoic acid in dimethylformamide (75 ml) at 5° C. were added 1.0 gm (7.41 mMol) 1-hydroxybenzotriazole, 1.42 ml (13.7 mMol) diethylamine and finally 1.53 gm (7.41 mMol) dicyclohexylcarbodiimide and the reaction mixture stirred at room temperature for 48 hours. The volatiles were removed under reduced pressure and the residue was purified by flash silica chromatography, eluting with 10% methanol in ethyl acetate. Fractions containing product were combined, concentrated under reduced pressure and the residue triturated with ethyl acetate to give 1.13 gm (34.9%) (−)-methyl 2-(1,5-dioxo-5-((phenylmethyl)amino)pentyl)amino-5-((imino(nitroamino)-methyl)amino)pentanoate.

m.p.=97°-99° C.
$[\alpha]_{589}(CH_3OH) = -8.89°$
Calculated for $C_{19}H_{28}N_6O_6$: Theory: C, 52.41; H, 6.25; N,19.30 Found: C, 52.13; H, 6.46; N,19.41

To a solution of 1.1 gm (2.58 mMol) (−)-methyl 2-(1,5-dioxo-5-((phenylmethyl)amino)pentyl)amino-5-((imino(nitroamino)methyl)amino)pentanoate in methanol (30 ml) and water (60 ml) was added 0.5 N sodium hydroxide (5.61 ml) and the solution was stirred at room temperature for one hour. The volatiles were removed under reduced pressure and the residue redissolved in water. The aqueous phase was washed once with ethyl acetate and the remaining aqueous phase was made acidic with 1N hydrochloric acid. This phase was then extracted with 3:1 n-butanol:toluene two times. The organic extracts were combined, dried over magnesium sulfate and concentrated under reduce pressure to give 700 mg (64.4%) of the title compound as a hygroscopic solid.

m.p.=60°-80° C.
ms (fd)=421($M^{30}$)
$[\alpha]_D(CH_3OH) = -6.17°$

Preparation VI

Synthesis of (−)-2-(1-oxo-4-((2-methyl-1-oxopropyl)-amino)butyl)amino-5-((imino(nitroamino)methyl-)amino)-pentanoic acid. [$(CH_3)_2CHC(O)NH(CH_2)_3$-$C(O)NHCH(CO_2H)$-$(CH_2)_3NHC(N)NHNO_2$].

To a solution of 20 gm (194 mMol) 4-aminobutanoic acid in dichloromethane (700 ml) were added 54 ml (407 mMol) triethylamine and the reaction mixture was stirred at room temperature for 10 minutes. To this mixture was then added a solution of 40.6 ml (407 mMol) isobutyryl chloride in dichloromethane (300 ml) dropwise and the resulting mixture was stirred at room temperature for 2 hours. The reaction mixture was filtered and the filtrate concentrated under reduced pressure. The residue was dissolved in 1N sodium hydroxide and stirred for 30 minutes. This solution was then poured into diethyl ether, diluted with water and the phases separated. The aqueous phase was acidified with hydrochloric acid and then extracted with ethyl acetate. The organic extracts were combined, dried over magnesium sulfate and concentrated under reduced pressure to give an oil. Bulb to bulb distillation (0.05 mm Hg, pot temperature=235° C.) gave 13.98 gm (43.1%) N-(2-methyl)propionyl-4-aminobutanoic acid.

Calculated for $C_8H_{15}NO_3$: Theory: C, 55.47; H, 8.73; N, 8.09 Found: C, 55.77; H, 8.98; N, 8.00

The N-(2-methyl)propionyl-4-aminobutanoic acid (1.28 gm) was converted to the title compound *(0.551 gm) by the procedure described in Preparation V. The title compound was recovered as a hygroscopic solid.

$[\alpha]_{589}(CH_3OH) = +0.79°$
ms (fd)=374 ($M^+ + 1$)

Preparation VII

Synthesis of 4-(trans-4-(3-hydroxyphenyl)-3,4-dimethyl-1-piperidinyl)-1-(cyclohexyl)-2-aminobutane. [$Q(CH_2)_2$-$CH(NH_2)CH_2(C_6H_{11})$.

To a solution of 60 gm (349 mMol) cyclohexylacetaldehyde dimethyl acetal in tetrahydrofuran (50 ml) and diethyl ether (100 ml) was added 1N hydrochloric acid (200 ml) and the resulting mixture was stirred for 2.5 hours at room temperature. The reaction mixture was then partitioned between diethyl ether and water. The ether layer was then separated, dried over magnesium sulfate and concentrated under reduced pressure to give 58 gm of crude cyclohexylacetaldehyde.

To a solution of this aldehyde in ethanol (200 ml) were added 39.9 gm (384 mMol) malonic acid and 53.8 gm (698 mMol) ammonium acetate. The mixture was then stirred at reflux for 20 hours. The reaction mixture was then evaporated to dryness under reduced pressure and the residue dissolved in 1N hydrochloric acid. The mixture was extracted once with ethyl acetate and the remaining aqueous phase was diluted with ammonium hydroxide to pH 9.8. This aqueous phase was then extracted with 3:1 butanol:toluene. The organic extract was dried over magnesium sulfate and the solvent removed under reduced pressure. The residue was purified by flash chromatography, eluting with a gradient system of ethyl acetate containing from 0–20% methanol. Fractions containing the desired 2-amino-4-cyclohexylbutanoic acid were concentrated under reduced pressure to give 5.67 gm of a colorless solid.

ms (fd)=186 ($M^+ + 1$)

The title compound was prepared by subjecting 2-amino-4-cyclohexylbutanoic acid (5.67 gm) to the sequence of reactions performed on 3-amino-3-phenylpropionic acid as described in Preparation II to provide 1.6 gm of product.

ms (fd)=359 ($M^+ + 1$)

Preparation VIII

Synthesis of 1-(trans-4-(3-hydroxyphenyl)-3,4-dimethyl-1-piperidinyl)-3-phenyl-2-aminopropane. [$Q$—$CH_2CH(NH_2)$-$CH_2(C_6H_5)$].

The title compound was prepared by subjecting DL-phenylalanine to the sequence of reactions performed on 3-amino-3-phenylpropionic acid as described in Preparation II to give a colorless foam.

ms (fd)=338 ($M^+$)339 ($M^+ + 1$)

Preparation IX

Synthesis of D-(+)- and D-(−)-1-(trans-4-(3-hydroxyphenyl)-3,4-dimethyl-1-piperidinyl)-3-phenyl-2-aminopropane. [$Q$—$(CH_2)CH(NH_2)CH_2(C_6H_5)$].

The title compound was prepared by subjecting D-phenylalanine to the sequence of reactions performed on 3-amino-3-phenylpropionic acid as described in Preparation II. Prior to the RedAl reduction of the corresponding 1-oxo derivatives of the title compound, the (+)- and (−)-diastereomers were isolatable by flash silica chromatography. The separation was accomplished by eluting with ethyl acetate (0–50% methanol). The (+)-diastereomer was the least polar of the two. Each diastereomer was reduced separately to give the corresponding amine.

D-(+)-(3R,4R,R)-1-(trans-4-(3-hydroxyphenyl)-3,4-dimethyl-1-piperidinyl)-3-phenyl-2-aminopropane (DIASTEREOMER A):

The title compound was recovered as a colorless foam.

ms (fd)=338($M^+$), 340($M^+ + 2$).
$[\alpha]_{365}(CH_3OH) = +202.18°$

D-(−)-(3S,4S,R)-1-(trans-4-(3-hydroxyphenyl)-3,4-dimethyl-1-piperidinyl)-3-phenyl-2-aminopropane (DIASTEREOMER B):

The title compound was recovered as a yellow foam.
ms (fd)=338(M+), 340(M++2).
$[\alpha]_{365}(CH_3OH) = -225.22°$

Preparation X

Synthesis of L-1-(trans-4-(3-hydroxyphenyl)-3,4-dimethyl-1-piperidinyl)-3-phenyl-2-aminopropane dihydrochloride. [Q-CH$_2$-CH(NH$_2$)CH$_2$(C$_6$H$_5$)].

The title compound was prepared by subjecting L-phenylalanine to the sequence of reactions performed on 3-amino-3-phenylpropionic acid as described in Preparation II. The title compound was recovered as a colorless foam.
m.p.=>196° C.(decomposition)
ms (fd)=338(M+), 339(M++1)
Calculated for C$_{22}$H$_{30}$N$_2$O.2HCl Theory: C, 64.23; H, 7.84; N, 6.81 Found: C, 63.95; H, 7.59; N, 6.70

Preparation XI

Synthesis of L-1-(trans-4-(3-hydroxyphenyl)-3,4-dimethyl-1-piperidinyl)-3-cyclohexyl-2-aminopropane. [Q-CH$_2$CH(NH$_2$)CH$_2$(C$_6$H$_{11}$)].

To a solution of 2.65 gm (10 mMol) L-N-tBOC-phenylalanine in ethanol (96 ml) was added 1.3 gm platinum oxide. The reaction vessel was then pressurized to 60 p.s.i. with hydrogen and the reaction mixture was stirred at room temperature for 3 hours. The reaction mixture was then filtered and the filtrate concentrated under reduced pressure. The L-N-tBOC-2-amino-3-cyclohexylpropionic acid (2.6 gm, 96%) was recovered as a colorless foam.
$[\alpha]_{589}(CH_3OH) = -8.24$
$[\alpha]_{365}(CH_3OH) = -21.77$
Calculated for C$_{14}$H$_{25}$NO$_4$: Theory: C, 61.97; H, 9.29; N,5.16 Found: C, 61.70: H, 9.03: N, 5.04

The title compound was prepared by subjecting L-N-tBOC-2-amino-3-cyclohexylpropionic acid to the sequence of reactions performed on 3-amino-3-phenylpropionic acid as described in Preparation II. The title compound was recovered as a colorless foam.
$[\alpha]_D(CH_3OH) = +73.12°$
ms (fd)=356 (M+)

Preparation XII

Synthesis of N-cyclohexyl-2-(trans-4-(3-hydroxyphenyl)-3,4-dimethyl-1-piperidinyl)ethylamine. [Q-(CH$_2$)$_2$NH-(C$_6$H$_{11}$)].

To a solution of 5.0 gm (24.3 mMol) trans-4-(3-hydroxyphenyl)-3,4-dimethylpiperidine in dimethylformamide (250 ml) were added 2.05 gm (26.7 mMol) sodium bicarbonate and 3.22 gm (26.7 mMol) bromoacetonitrile. The reaction mixture was stirred at reflux for 1.5 hours and the solvent then removed under reduced pressure. The residue was partitioned between ethyl acetate and water and the aqueous phase was then adjusted to pH=9.8 with 1N aqueous sodium hydroxide. The phases were separated and the aqueous phase was extracted with ethyl acetate. All of the ethyl acetate extracts were combined, dried over potassium carbonate and the volatiles removed under reduced pressure to give 6.0 gm of trans-4-(3-hydroxyphenyl)-3,4-dimethyl-1-piperidinylacetonitrile as a yellow viscous oil. A portion of this oil was converted to the corresponding hydrochloride salt which was recovered as a colorless solid.
m.p.=210°-211° C.
Calculated for C$_{14\text{5}}$H$_{20}$N$_2$O.HCl: Theory: C, 64.16; H, 7.54; N, 9.98 Found: C, 64.11; H, 7.53; N, 9.79

To a solution of 35 ml (100 mMol) RedAl (3.5 M in toluene) was added dropwise a solution of 6.0 gm (24.3 mMol) trans-4-(3-hydroxyphenyl)-3,4-dimethyl-1-piperidinylacetonitrile in toluene (100 ml). The resulting solution was stirred for 1 hour at 60° C. The reaction mixture was then cooled to room temperature and then poured into a slurry of ice/water buffered to pH 10.00. The aqueous phase was adjusted to pH of 9.8 with 1N hydrochloric acid and the mixture then extracted with 3:1 butanol:toluene. The organic phases were combined, dried over potassium carbonate and the volatiles removed under reduced pressure. The solid residue was crystallized from ethyl acetate/hexane (1:1) to give 3.5 gm (57.6%) 2-(trans-4-(3-hydroxyphenyl)-3,4-dimethyl-1-piperidinyl)ethylamine as a colorless solid.
m.p.=114°-115° C.

The mother liquors from the crystallization were purified by silica gel chromatography. Fractions shown to contain product were combined and concentrated under reduced pressure to give colorless crystals which were slurried in hexane and filtered to give an additional 1.1 gm (18.1%) the desired 2-(trans-4-(3-hydroxyphenyl)-3,4-dimethyl-1-piperidinyl)ethylamine.
m.p.=129°-130° C.
Calculated for C$_{15}$H$_{24}$N$_2$O: Theory: C, 72.54; H, 9.74; N, 11.28 Found: C, 72.34; H, 9.69; N, 11.48

A solution of 1.0 gm (4 mMol) 2-(trans-4-(3-hydroxyphenyl)-3,4-dimethyl-1-piperidinyl)ethylamine in a minimal volume of methanol was saturated with hydrogen chloride. The volatiles were removed under reduced pressure to give 1.38 gm of the corresponding dihydrochloride salt. To a solution of this salt in methanol (12 ml) was added 71 mg (1.26 mMol) potassium hydroxide and the solution was stirred until the hydroxide dissolved. To this solution was then added 423 mg (4.3 mMol) cyclohexanone and the mixture stirred for 30 minutes at room temperature. To this mixture was added a solution of 105 mg (1.67 mMol) sodium cyanoborohydride in methanol (10 ml) and the reaction mixture was stirred for an additional 30 minutes. An additional 70 mg (1.26 mMol) potassium hydroxide were added and the reaction mixture stirred for 15 minutes. The reaction mixture was then poured into a slurry of ice/water and the pH adjusted to 9.8 with 1N NaOH. The mixture was then extracted with 3:1 butanol:toluene. The organic extracts were combined, dried over potassium carbonate and concentrated under reduced pressure. The residue was purified by silica gel chromatography, eluting with methanol. Fractions containing product were combined and concentrated under reduced pressure. The residue was triturated with ethyl acetate and the resulting solid crystallized from ethyl acetate/hexane (1:1) to give the title compound as a colorless crystalline solid (830 mg, 62.9%).
m.p.=143°-145° C.
Calculated for C$_{21}$H$_{34}$N$_2$O: Theory: C, 76.31; H, 10.37; N,8.48 Found: C, 76.11; H, 10.51; N, 8.52

Preparation XIII

Synthesis of N-cyclopentyl-2-(trans-4-(3-hydroxyphenyl)-3,4-dimethyl-1-piperidinyl)ethylamine. [Q-(CH$_2$)$_2$gNH(C$_5$H$_9$)].

A solution of 2.00 gm (8 mMol) 2-(trans-4-(3-hydroxyphenyl)-3,4-dimethyl-1-piperidinyl)ethylamine in a minimal volume of methanol was contacted with 656 mg (8 mMol) cyclopentanone according to the procedure described in Preparation XII. The title compound was recovered as a colorless crystalline solid (1.21 gm, 47.9%).

m.p. = 150°–152° C.
ms (fd) = 316(M+)

Calculated for $C_{20}H_{32}N_2O$: Theory: C, 75.90; H, 10.19; N, 8.85 Found: C, 75.73; H, 10.14; N, 8.67

Preparation XIV

Synthesis of N-cyclohexyl-3-(trans-4-(3-hydroxyphenyl)-3,4-dimethyl-1-piperidinyl)propylamine. [Q-$(CH_2)_3$NH-$(C_6H_{11})$].

The procedure of Preparation II was followed.

A. Preparation of N-tBOC-N-cyclohexyl-3-aminopropionic acid

The following materials were used:
N-cyclohexyl-3-aminopropionic acid (19 gm)
Dioxane (382 ml)
Water (191 ml)
Aqueous 1N sodium hydroxide (191 ml)
Di-tert-butyl dicarbonate (47 gm) to give 10.26 gm of product recrystallized from hexane.

m.p. = 104°–105° C.

Calculated for $C_{14}H_{25}NO_4$: Theory: C, 61.97; H, 9.29; N, 5.16 Found : C, 61.68; H, 9.02; N, 5.27

B. Preparation of trans-1-(N-tBOC-N-cyclohexyl-3-aminopropionyl)-4-(3-hydroxyphenyl)-3,4-dimethylpiperidine The following materials were used:
trans-4-(3-hydroxyphenyl)-3,4-dimethylpiperidine (2.0 gm)
N-tBOC-N-cyclohexyl-3-aminopropionic acid (2.64 gm)
DCC (2.013 gm)
HOBT (1.318 gm)
DMF (100 ml)

4.5 gm of product were obtained.
ms (fd) = 441 (M+ +1)

C. Preparation of trans-1-(N-cyclohexyl-3-aminopropionyl)-4-(3-hydroxyphenyl)-3,4-dimethylpiperidine The following materials were used:
Product from B above (4.54 gm)
6N HCl (200 ml)

2.8 gm of product were recovered.
ms (fd) = 359 (M+ +1)

D. Preparation of 1-(N-cyclohexyl-3-aminopropionyl)-4-(3-hydroxyphenyl)-3,4-dimethylpiperidine The following materials were used:
RedAl (9 ml, 3.4 molar in toluene)
Toluene (100 ml)
Product from C above (2.8 gm) in toluene (70 ml)

2.62 gm of product were recovered.
ms (fd) = 262 (M+), 263 (M+ +1)

Preparation XV

Synthesis of 3-(trans-4-(3-hydroxyphenyl)-3,4-dimethyl-1-piperidinyl)propylamine. [Q-$(CH_2)_3NH_2$].

The sequence of reactions described in Preparation II were followed.

A. Preparation of trans-1-(N-tBOC-3-aminopropionyl)-4-(3-hydroxyphenyl)-3,4-dimethylpiperidine The following materials were used:
N-tBOC-3-aminopropionic acid (2.76 gm)
Trans-4-(3-hydroxyphenyl)-3,4-dimethylpiperidine (3 gm)
HOBT (2.38 gm)
DCC (3 gm)
Dimethylformamide (150 ml)

6.36 gm of product were obtained

B. Hydrolysis of t-BOC 6N HCl (200 ml)

C. Formation of title compound

The following materials were used:
Product from B above (5.25 gm)
Toluene (300 ml)
RedAl (30 ml)

Inverse addition was required due to solubility. 3.1 gm of product were recovered.
ms (fd) = 263 (M+ +1)

Preparation XVI

Synthesis of N-phenyl-2-(trans-4-(3-hydroxyphenyl)-3,4-dimethyl-1-piperidinyl)ethylamine. [Q-$(CH_2)_2$NH$(C_6H_5)$].

To a solution of 2.0 gm (9.72 mMol) trans-4-(3-hydroxyphenyl)-3,4-dimethylpiperidine and 1.48 gm (9.72 mMol) N-phenylglycine in dimethylformamide (200 ml) at 5° C. were added sequentially 1.32 gm (9.72 mMol) 1-hydroxybenzotriazole and 2.02 gm (9.72 mMol) dicyclohexylcarbodiimide and the reaction mixture stirred at room temperature for 72 hours. The reaction mixture was cooled to 0° C., filtered and the filtrate was concentrated under reduced pressure. The residue was purified by silica gel chromatography, eluting with ethyl acetate. Fractions containing N-phenyl-2-(trans-4-(3-hydroxyphenyl)-3,4-dimethyl-1-piperidinyl)-2-oxo-ethylamine were combined and concentrated under reduced pressure to give 3.11 gm (94.7%) of a colorless foam.

ms (fd) = 338(M+)

To a solution of 10 ml (35 mMol) RedAl (3.5 M in toluene) was added a solution of 3.0 gm (8.87 mMol) N-phenyl-2-(trans-4-(3-hydroxyphenyl)-3,4-dimethyl-1-piperidinyl)-2-oxo-ethylamine in toluene (100 ml) dropwise. The reaction mixture was then stirred for 1 hour at 60° C. The solution was cooled to room temperature and poured into an ice/water buffered to pH 10.00. The pH of the aqueous phase was adjusted to 9.8 with 1N HCl and the mixture was extracted well with 3:1 butanol:toluene. The organic phases were combined, dried over potassium carbonate and concentrated under reduced pressure. The residue is purified by silica gel chromatography, eluting with ethyl acetate. Fractions containing the title compound are combined and concentrated under reduced pressure. Crystalline residue is slurried in hexane and filtered to give the title compound as a white crystalline solid (2.2 gm, 76.6%).

m.p. = 112°–113° C.
ms (fd) = 324(M+)

Calculated for $C_{21}H_{27}N_2O$: Theory: C, 77.74; H, 8.70; N, 8.63 Found: C, 77.84; H, 8.92; N, 8.34

Preparation XVII

Synthesis of N-phenyl-3-[trans-4-(3-hydroxyphenyl)-3,4-dimethyl-1-piperidinyl]propylamine. [Q-$(CH_2)_3$NH$(C_6H_5)$].

The procedure of Preparation XVI was followed with the following materials:
N-phenyl-3-aminopropionic acid (1.65 gm, 10 mMol),
trans-4-(3-hydroxyphenyl)-3,4-dimethylpiperidine (1.65 gm)
HOBT (1.35 gm)
DCC (2.06 gm)
DMF (100 ml)

2.0 gm of N-phenyl-3-[trans-4-(3-hydroxyphenyl)-3,4-dimethyl-1-piperidinyl]-2-oxo-propylamine were recovered.

ms (fd) = 351 (M+)

This product was reduced (1.66 gm) in toluene (100 ml) with RedAl (10 ml) to provide 500 mg of title product.

ms (fd) = 338 (M+)

Preparation XVIII

Synthesis of N-cyclohexylmethyl-2-(trans-4-(3-hydroxyphenyl)-3,4-dimethyl-1-piperidinyl)ethylamine. [Q-$(CH_2)_2$-NHCH$_2(C_6H_{11})$].

The sequence of reactions described in Preparation XVI were used with the following materials to provide the title compound.

2-trans-4-(3-hydroxyphenyl)-3,4-dimethyl-1-piperidinyl)ethylamine (1.0 gm)
cyclohexylcarboxylic acid (512 mg)
HOBT (540 mg)
DCC (824 mg)
DMF (60 ml)

1.38 gm of N-(cyclohexylcarbonyl)-2-(trans-4-(3-hydroxyphenyl)-3,4-dimethyl-1-piperidinyl)ethylamine were recovered.

ms (fd) = 358 (M+), 359 (M+ +1)
IR: 1671.3 cm$^{-1}$ (C=O)

This product (1.3 gm) in toluene (100 ml) was reduced with RedAl (12 ml) using inverse addition to provide 280 mg of product.

ms (fd) = 344 (M+), 345 (M+ +1)

Preparation XIX

Synthesis of N-cyclohexylmethyl-3-(trans-4-(3-hydroxyphenyl)-3,4-dimethyl-1-piperidinyl)propylamine. [Q-$(CH_2)_3$NHCH$_2(C_6H_{11})$].

A 1.42 gm (5.4 mMol) portion of 3-(trans-4-(3-hydroxyphenyl)-3,4-dimethyl-1-piperidinyl)propylamine [Preparation XV] and 692 mg (5.4 mMol) cyclohexanecarboxylic acid were subjected to the sequence of reactions described in Preparation XVI to give the title compound as a colorless foam.

ms (fd) = 358(M+)

Preparation XX

Synthesis of N-(3-methyl)butyl-2-(trans-4-(3-hydroxyphenyl)-3,4-dimethyl-1-piperidinyl)ethylamine. [Q-$(CH_2)_2$NH$(CH_2)_2$CH$(CH_3)_2$].

An 800 mg (3.2 mMol) portion of 2-(trans-4-(3-hydroxyphenyl)-3,4-dimethyl-1-piperidinyl)ethylamine [Preparation XII] and 337 mg (3.2 mMol) 3-methylbutanoic acid were subjected to the sequence of reactions described in Preparation XVI to give the title compound as a colorless foam.

ms (fd) = 318(M+), 319(M+ +1)

Preparation XXI

Synthesis of N-(2-methyl)propyl-3-(trans-4-(3-hydroxyphenyl)-3,4-dimethyl-1-piperidinyl)propylamine. [Q-$(CH_2)_3$-NHCH$_2$CH$(CH_3)_2$].

A 1.42 gm (5.4 mMol) portion of 3-(trans-4-(3-hydroxyphenyl)-3,4-dimethyl-1-piperidinyl)propylamine [Preparation XV] and 475 mg (5.4 mMol) 2-methylpropanoic acid were subjected to the sequence of reactions described in Preparation XVI to give the title compound as a colorless foam.

ms (fd) = 318(M+)

EXAMPLE 1

4-[(3-(4-(3-hydroxyphenyl)-3,4-dimethyl-1-piperidinyl)-1-(cyclohexylmethyl)propyl)amino]-4-oxobutanoic acid monohydrate [Q-$(CH_2)_2$CH[CH$_2(C_6H_{11})$]NHC(O)(CH$_2)_2$C(O)-OH].

To a solution of 500 mg (1.33 mMol) 3-(trans-4-(3-hydroxyphenyl)-3,4-dimethyl-1-piperidinyl)-1-(cyclohexylmethyl)propylamine (Prep VII) in dimethylformamide (50 ml) were added 199 mg (1.99 mMol) of succinic anhydride and the reaction mixture was stirred at room temperature for 3 days. Volatiles were removed under reduced pressure and the residue was purified by flash silica chromatography, eluting with 1:1 ethyl acetate methanol. Fractions containing product were concentrated under reduced pressure and the solid residue was crystallized from ethyl acetate. The title compound was isolated as a crystalline solid (270 mg, 42.6%).

m.p. = 117°–120° C.

Calculated for $C_{27}H_{42}N_2O_4 \cdot H_2O$: Theory: C, 68.04; H, 9.30; N, 5.87 Found: C, 68.08; H, 9.02; N, 5.91

EXAMPLE 2

4-[[1-[2-[4-(3-hydroxyphenyl)-3,4-dimethyl-1-piperidinyl]-ethyl]-3-methylbutyl)amino]-4-oxobutanoic acid ethyl ester. [Q-$(CH_2)_2$CH[CH$_2$CH(CH$_3)_2$]NHC(O)(CH$_2)_2$-C(O)OCH$_2$CH$_3$].

To a solution of 1.0 gm (3.13 mMol) of trans-1-(4-(3-hydroxyphenyl)-3,4-dimethyl-1-piperidinyl)-3-amino-5-methylhexane (Prep IV) in dimethylformamide (50 ml) were added sequentially 450 mg (3.13 mMol) monoethyl succinate, 420 mg (3.13 mMol) 1-hydroxybenzotriazole and 640 mg (3.13 mMol) dicyclohexylcarbodiimide. The reaction mixture was allowed to stir for 72 hours at room temperature. The reaction mixture was concentrated under reduced pressure and the residue was partitioned between ethyl acetate and water. The solution was adjusted to pH = 9.8 with 1N sodium hydroxide and the layers separated. The organic phase was washed with water, dried over potassium carbonate and concentrated under reduced pressure to give a solid residue which was purified by high pressure liquid chromatography, eluting with 20% methanol in ethyl acetate. Two pairs of diastereomers were separated by the chromatography. The least polar pair of diastereomers (A) recovered was isolated as the hydrochloride salt (520 mg, 34%).

m.p. = 65°–75° C.

Calculated for $C_{26}H_{42}N_2O_4 \cdot HCl$: Theory: C, 64.64; H, 8.97; N, 5.80 Found: C, 64.44; H, 8.94; N, 5.94

The second pair of diastereomers (B) recovered was isolated as a hydrate of the free base (260 mg, 17.8%).

m.p. = 70°–85° C.

Calculated for $C_{26}H_{42}N_4O_4 \cdot H_2O$: Theory: C, 62.32; H, 9.05; N, 5.59 Found: C, 62.60; H, 8.88; N, 5.58

EXAMPLE 3

5-((1-(2-(trans-4-(3-hydroxyphenyl)-3,4-dimethyl-1-piperidinyl)ethyl)-3-methylbutyl)amino)-5-oxopentanoic acid ethyl ester monohydrochloride (232959). [Q-$(CH_2)_2$-CH[CH$_2$CH(CH$_3)_2$]NHC(O)(CH$_2)_3$-C(O)OCH$_2$CH$_3 \cdot$HCl].

A solution of 1.0 gm (3.13 mMol) of trans-1-(4-(3-hydroxyphenyl)-3,4-dimethyl-1-piperidinyl)-3-amino-5-methylhexane (Prep IV) in dimethylformamide (50 ml) was reacted with 500 mg (3.13 mMol) mono-ethyl glutarate under the conditions described in Example 2. The least polar pair of diastereomers was isolated as the hydrochloride salt (390 mg, 25%).

m.p.=65°-68° C.

Calculated for $C_{27}H_{44}N_2O_4 \cdot HCl$: Theory: C, 65.24; H, 9.12; N, 5.64 Found: C, 65.45; H, 8.82; N, 5.68

The second pair of diastereomers (B) recovered was also isolated as the hydrochloride salt (255 mg, 16.3%).

m.p.=50°-70° C.

Calculated for $C_{27}H_{46}ClN_2O_4$: Theory: C, 65.24; H, 9.12; N, 5.64 Found: C, 64.91; H, 8.97; N, 5.34

EXAMPLE 4

5-[[1-(2-methylpropyl)-3-[4-(3-hydroxyphenyl)-3,4-dimethyl-1-piperidinyl]propyl]amino]-5-oxopentanoic acid. [Q-$(CH_2)_2CH[CH_2CH(CH_3)_2]NHC(O)(CH_2)_3$-$C(O)OH$].

Trans-1-(4-(3-hydroxyphenyl)-3,4-dimethyl-1-piperidinyl)-3-amino-5-methylhexane (400 mg, 1.25 mMol) (Prep IV) was contacted with glutaric anhydride (158 mg, 1.38 mMol) and the mixture stirred for 18 hours. The solvent was removed and the residue was purified by silica column chromatography eluting with ethanol/methanol 1:1. After removal of solvent from fractions containing product, the product was dissolved in hot acetonitrile and filtered. The acetonitrile was removed by vacuum and the solid recrystallized from ethyl acetate to give the title compound as a crystalline solid (300 mg, 55.5%).

m.p=65°-71° C.

Calculated for $C_{25}H_{40}N_2O_4$: Theory: C. 69.41; H, 9.32; N, 6.48 Found: C, 69.18; H, 9.07; N, 6.38

EXAMPLE 5

5-((3-(trans-4-(3-hydroxyphenyl)-3,4-dimethyl-1-piperidinyl)-1-cyclohexylpropyl)amino)-5-oxo-pentanoic acid monohydrochloride monohydrate. (Q-$(CH_2)_2CH(C_6H_{11})NHC(O)(CH_2)_3C(O)OH \cdot HCl \cdot H_2O$].

Trans-3-(4-(3-hydroxyphenyl)-3,4-dimethyl-1-piperidinyl)-1-cyclohexylpropylamine (800 mg, 2.32 mMol) (Prep III) was treated with glutaric anhydride and stirred overnight. The solvent was removed and the residue was passed through a silica column eluting with ethyl acetate and methanol (1:1). The recovered residue was heated in a mixture of acetonitrile and methanol (1:1), filtered and the solvent removed. The residue was taken into acetonitrile, filtered and the acetonitrile removed to provide a white solid.

m.p.=120°-130° C.

ms (fd)=460 (M+)

The residue was converted to the HCl salt and triturated with ethyl ether to provide the hydrochloride salt as a monohydrate (410 mg, 38.5%).

m.p.=80°-90° C.

ms (fd)=460 (M++1)

Calculated for $C_{27}H_{42}N_2O_4 \cdot HCl \cdot H_2O$: Theory: C,63.20; H, 8.77; N, 5.45 Found: C,63.06; H, 8.37; N, 5.46

EXAMPLE 6

N-(3-(trans-4-(3-hydroxyphenyl)-3,4-dimethyl-1-piperidinyl)-1-phenylpropyl)acetamide. [Q-$(CH_2)_2$-$CH(C_6H_5)NHC(O)CH_3$].

To a solution of 870 mg (2.57 mMol) 3-(trans-4-(3-hydroxyphenyl)-3,4-dimethyl-1-piperidinyl)-1-phenylpropylamine (Prep II) in dichloromethane (30 ml) were added 0.71 ml (5.13 mMol) triethylamine followed by 0.36 ml (5.13 mMol) acetyl chloride and the solution was stirred at room temperature for 1 hour. The volatiles were removed under reduced pressure and the residue partitioned between water and ethyl acetate. The pH of the mixture was adjusted to 9.8 with 1N sodium hydroxide and the phases separated. The organic phase was dried over potassium carbonate and concentrated under reduced pressure to give 1.2 gm (100+%) crude N-(3-(trans-4-(3-acetoxyphenyl)-3,4-dimethyl-1-piperidinyl)-1-phenylpropyl)acetamide.

To a solution of 1.2 gm N-(3-(trans-4-(3-acetoxyphenyl)-3,4-dimethyl-1-piperidinyl)-1-phenylpropyl)-acetamide in methanol (50 ml) was added 25% aqueous sodium hydroxide (50 ml) and the solution was stirred at room temperature for 2 hours. The volatiles were removed under reduced pressure and an aqueous solution of the residue adjusted to pH 9.8 with 10% hydrochloric acid. The mixture was then extracted with 3:1 butanol:toluene. The organic phases were combined, dried over magnesium sulfate and concentrated under reduced pressure to give 1.1 gm of a solid residue. The residue was triturated with hexane and the filtered solid purified by flash silica chromatography eluting with ethyl acetate/methanol (1:1) to give the title compound as a solid (320 mg, 16.4%).

m.p.=78°-85° C.

Calculated for $C_z<H_{32}N_2O_z$: Theory: C, 75.75; H, 8.48; N, 7.36 Found: C, 75.45; H, 8.37; N, 7.08

EXAMPLE 7

5-((1-(cyclohexylmethyl)-3-(trans-4-(3-hydroxyphenyl)-3,4-dimethyl-1-piperidinyl)propyl)amino)-5-oxopentanoic acid monohydrochloride monohydrate. [Q-$(CH_2)_2CH$-$[CH_2(C_6H_{11})]NHC(O)(CH_2)_3$-$C(O)OH \cdot HCl \cdot H_2O$].

4-(Trans-4-(3-hydroxyphenyl)-3,4-dimethyl-1-piperidinyl)-1-(cyclohexyl)-2-aminobutane (500 mg, 1.39 mMol) [Preparation VII] was treated with glutaric anhydride and the title compound isolated under the conditions described in Example 1. The title compound was isolated as a hydrochloride salt monohydrate (500 mg, 68.4%).

m.p.=95°-100° C.

Calculated for $C_{28}H_{44}N_2O_4 \cdot HCl \cdot H_2O$: Theory: C, 63.80; H, 8.99; N, 5.31 Found: C, 63.54; H, 8.93; N, 4.94

EXAMPLE 8

(−)-N-(1-phenyl-3-(trans-4-(3-hydroxyphenyl)-3,4-dimethyl-1-piperidinyl)propyl)-2-((1,5-dioxo-5-(phenylmethyl)amino)pentyl)amino-5-((imino(nitroamino)methyl)-amino)pentanamide. [Q-$(CH_2)_2CH(C_6H_5)NHC(O)CH[(CH_2)_3$-$NHC(NH)NHNO_2]NHC(O)(CH_2)_3$-$C(O)NHCH_2(C_6H_5)$].

3-(Trans-4-(3-hydroxyphenyl)-3,4-dimethyl-1-piperidinyl)-1-phenylpropylamine (500 mg, 1.47 mMol) (Prep II) and (−)-2-(1,5-dioxo-5-((phenylmethyl)amino)-pentane)-5-((imino(nitroamino)methyl)amino)-pentanoic acid [Preparation V] (622 mg, 1.47 mMol) were coupled following the procedure of Example 2 to give the title compound (386 mg, 35.3%).

m.p.=100°-105° C. (foam)

$[\alpha]_{589}(CH_3OH) = -3.546°$ $[\alpha]_{365}(CH_2OH) = -7.092$

Calculated for $C_{40}H_{54}N_8O_6$: Theory: C, 64.76; H, 7.20; N, 15.10 Found: C, 65.05; H, 7.50; N, 14.93

EXAMPLE 9

(−)-N-(1-phenyl-3-(trans-4-(3-hydroxyphenyl)-3,4-dimethyl-1-piperidinyl)propyl)-2-((1-oxo-4-(2-methyl-1-oxopropyl)amino) butyl)amino-5-((imino(nitroamino)-methyl)amino)pentanamide. [Q-(CH$_2$)$_2$CH(C$_6$H$_5$)NHC(O)CH-[(CH$_2$)$_3$NHC(NH)NHNO$_2$]NHC(O)(CH$_2$)$_3$NHC(O)CH(CH$_3$)$_2$].

3-(trans-4-(3-hydroxyphenyl)-3,4-dimethyl-1-piperidinyl)-1-phenylpropylamine (500 mg, 1.47 mMol) (Prep II) and (−)-2-(1-oxo-4-((2-methyl-1-oxopropyl)-amino)butyl)amino-5-((imino(nitroamino)methyl)-amino)-pentanoic acid [Preparation VI] (550 mg, 1.47 mMol) were coupled as described in Example 2 except the mixture was stirred for 48 hours and the residue was dissolved in 3:1 butanol/toluene prior to purification by chromatography. The title compound (170 mg, 15.8%) was recovered as the hydrochloride salt.

m.p.=130°-150° C. (decomposition)
[α]$_D$(CH$_5$OH)=−6.69°
Calculated for C$_{36}$H$_{54}$N$_8$O$_6$.HCl: Theory: C, 59.21; H, 7.45; N, 15.34 Found: C, 58.94; H, 7.67; N, 15.10

EXAMPLE 10

Ethyl trans-(3R,4R,R)-3-((2-(4-(3-hydroxyphenyl)-3,4-dimethyl-1-piperidinyl)-1-(D-(phenylmethyl)ethyl-)amino))-3-oxopropionate hydrochloride (DIASTEREOMER A) [Q-CH$_2$CH[CH$_2$-(C$_6$H$_5$)NHC(O)CH$_2$-C(O)OCH$_2$CH$_3$.HCl].

To a solution of 500 mg (1.S mMol) D-(+)-1-(trans-4-(3-hydroxyphenyl)-3,4-dimethyl-1-piperidinyl)-3-phenyl-2-aminopropane (Diastereomer A from [Preparation IX]) and 152 mg (1.5 mMol) triethylamine in dichloromethane (40 ml) was added a solution of 226 mg (1.5 mMol) ethyl malonyl chloride in dichloromethane (10 ml) dropwise at 0° C. The reaction mixture was allowed to stir for 1 hour at 0° C. and then for an additional 2 hours at room temperature. The reaction mixture was then concentrated to dryness under reduced pressure. The residue was dissolved in 3:1 butanol toluene and washed with saturated aqueous sodium chloride. The remaining organic phase was dried over potassium carbonate and concentrated under reduced pressure. The residue was purified by silica gel chromatography, eluting with a gradient system of hexane containing 10-100% ethyl acetate. Fractions containing the desired product were combined, concentrated under reduced pressure and the residue converted to the hydrochloride salt to give the title compound (400 mg, 54.5%) as a colorless solid.

m.p.=89°-93° C.
ms (fd)=452(M+)
[α]$_{365}$(CH$_3$OH)=+22.46°
Calculated for C$_{27}$H$_{36}$N$_2$O$_4$.HCl: Theory: C, 66.31; H, 7.63; N, 5.73 Found: C, 66.09; H, 7.78; N, 5.61

EXAMPLE 11

Trans-3-((2-(4-(3-hydroxyphenyl)-3,4-dimethyl-1-piperidinyl)-1-(D-(phenylmethyl)ethyl)amino))-3-oxopropionic acid (DIASTEREOMER A) (QCH$_2$CH[CH$_2$(C$_6$H$_5$)]NHC(O)CH$_2$C(O)OH].

To a solution of 700 mq (1.57 mMol) ethyl trans-3-((2-(4-(3-hydroxyphenyl)-3,4-dimethyl-1-piperidinyl)-1-(D-(phenylmethyl)ethyl)amino)-3-oxopropionate (prepared as in Example 10) in methanol (50 ml) were added 430 mg (3.14 mMol) potassium carbonate and the mixture was stirred at room temperature for 3 hours. The reaction mixture was filtered and the volatiles removed at room temperature. The residue was purified by silica gel chromatography, eluting with a gradient system of ethyl acetate containing 10-50% methanol to give the title compound as a colorless solid (500 mg, 75.1%).

m.p.=119°-123° C.
ms (fd)=424(M+), 425(M++1)
[α]$_{365}$(CH$_3$OH)=(+)48.71°
Calculated for C$_{25}$H$_{32}$N$_2$O$_4$ Theory: C, 70.73; H, 7.60; N, 6.60 Found: C, 70.42; H, 7.40; N, 6.47

EXAMPLE 12

Ethyl trans-3-((2-(4-(3-hydroxyphenyl)-3,4-dimethyl-1-piperidinyl)-1-(D-(phenylmethyl)ethyl)amino))-3-oxopropionate hydrochloride (DIASTEREOMER B) [Q-CH$_2$CH[CH$_2$(C$_6$H$_5$)]NHC(O)CH$_2$-C(O)OCH$_2$CH$_3$.HCl].

1.0 gm (3.0 mMol) D-(−)-1-(trans-4-(3-hydroxyphenyl)-3,4-dimethyl-1-piperidinyl)-3-phenyl-2-aminopropane (Diastereomer B from Preparation IX) was subjected to the reaction conditions described in Example 10 to give the title compound as a colorless solid (200 mg, 13.6%).

m.p.=95°-98° C.
ms (fd)=452(M+), 453(M++1).
[α]$_{365}$(CH$_3$OH)=−150°
Calculated for C$_{27}$H$_{36}$N$_2$O$_4$.HCl: Theory: C, 66.31; H, 7.63; N, 5.73 Found: C, 66.12; H, 7.41; N, 5.51

EXAMPLE 13

Trans-3-((2-(4-(3-hydroxyphenyl)-3,4-dimethyl-1-piperidinyl)-1-(D-(phenylmethyl)ethyl)amino))-3-oxopropionic acid monohydrate (DIASTEREOMER B). [Q-CH$_2$CH[CH$_2$(C$_6$H$_5$)]-NHC(O)CH$_2$-C(O)OH].

To a solution of 630 mg (1.4 mMol) ethyl trans-3-((2-(4-(3-hydroxyphenyl)-3,4-dimethyl-1-piperidinyl)-1-(D-(phenylmethyl)ethyl)amino))-3-oxopropionate (prepared as in Example 12) in a solvent mixture of tetrahydrofuran (18 ml), methanol (6 ml) and water (6 ml) were added 176 mg (4.2 mMol) lithium hydroxide and the reaction mixture was allowed to stir at room temperature for 3 hours. The reaction mixture was then poured into 10% hydrochloric acid, diluted with water and extracted with 3:1 butanol:toluene. The organic extracts were combined, washed with water, dried over magnesium sulfate and concentrated under reduced pressure. The residue was purified by silica gel chromatography, eluting with a gradient system of ethyl acetate containing 0-50% methanol. Fractions containing product were combined and concentrated under reduced pressure to give 430 mg (69.4%) of the title compound as a colorless solid.

m.p.=137°-140° C.
ms (fd)=424(M+), 425(M++1)
[α]$_{365}$(CH$_3$OH)=−248°
Calculated for C$_{25}$H$_{34}$N$_2$O$_5$: Theory: C, 67.85; H, 7.60; N, 6.60 Found: C, 67.55; H, 7.76; N, 6.48

EXAMPLE 14

[2-(trans-4-(3-hydroxyphenyl)-3,4-dimethyl-1-piperidinyl) -1-phenylmethyl-ethylamino]-4-oxobutanoic acid. [QCH$_2$CH[CH$_2$(C$_6$H$_5$)]NHC(O)(CH$_2$)$_2$-C(O)OH.

A solution of 700 mg (2.1 mMol) DL-1-(trans-4-(3-hydroxyphenyl)-3,4-dimethyl-1-piperidinyl)-3-phenyl-2-aminopropane [Preparation VIII] and 220 mg (2.2 mMol) succinic anhydride in dichloromethane (50 ml)

were combined and stirred at room temperature for 3 hours. The mixture was filtered and the solid was recrystallized from an ethyl acetate, acetone, water (5:4:1) mixture to provide the title compound as a colorless solid (170 mg, 18.4%).

m.p. = 162.5°–164° C.

ms (fd) = 438(M+), 439(M+ +1)

Calculated for $C_{26}H_{34}N_2O_4$: Theory: C, 71.21; H, 7.81; N, 6.39 Found: C, 70.97; H, 7.70; N, 6.09

EXAMPLE 15

Trans-5-((2-(4-(3-hydroxyphenyl)-3,4-dimethyl-1-piperidinyl)-1-(D-(phenylmethyl)ethyl)amino))-5-oxopentanoic acid monohydrate. [Q-$CH_2CH[CH_2(C_6H_5)]$-NHC(O)$(CH_2)_3$C(O)OH].

A solution of 500 mg (1.5 mMol) (+)-1-(trans-4-(3-hydroxyphenyl)-3,4-dimethyl-1-piperidinyl)-3-phenyl-2-aminopropane Preparation VIII and 188 mg (1.5 mMol) glutaric anhydride in dimethylformamide (50 ml) were stirred overnight at room temperature. The mixture was evaporated to dryness and the solid passed through a silica column eluting with an ethyl acetate to methanol gradient solvent. The title compound was isolated after recrystallization from acetonitrile water (9:1) as a colorless solid (370 mg, 52.4%).

m.p. = 98.5°–101° C.

ms (fd) = 452(M+), 453(M+ +1)

Calculated for $C_{27}H_{36}N_2O_4 \cdot H_2O$: Theory: C, 68.84; H, 8.09; N, 5.95 Found: C, 68.98; H, 7.92; N, 6.17

EXAMPLE 16

(+)-5-[[2-cyclohexyl-1-[[trans-4-(3-hydroxyphenyl)-3,4-dimethyl-1-piperidinylmethyl]ethyl]amino]-5-oxopentanoic acid. [Q-$CH_2CH[CH_2(C_6H_{11})]NHC(O)(CH_2)_3C(O)OH$].

A solution of 600 mg (1.7 mMol) (+)-1-(trans-4-(3-hydroxyphenyl)-3,4-dimethyl-1-piperidinyl)-3-cyclohexyl-2-amino-propane [Preparation XI] and 225 mg (1.9 mMol) glutaric anhydride in dimethylformamide (50 ml) were stirred at room temperature for 24 hours. The solvent was evaporated and the residue was purified by silica gel chromatography, eluting with ethyl acetate containing 30% methanol, to give the title compound (410 mg) (52.6%).

m.p = 100°–115° C. (foam)

$[\alpha]_{589}(CH_3OH) = +23.54°$ $[\alpha]_{365}(CH_3OH) = +78.34°$

Calculated for $C_{27}H_{42}N_2O_4$: Theory: C, 70.71; H, 9.23; N, 6.11 Found: C, 70.47; H, 9.43; N, 6.07

The material prepared above was converted to the corresponding hydrochloride monohydrate by adding methanolic hydrogen chloride to a methanol solution of the above described free base until the solution was acidic to pH paper. The volatiles were then removed under reduced pressure and the residue triturated with diethyl ether. The title compound was recovered as a colorless solid.

m.p. = 95°–100° C.

Calculated for $C_{27}H_{42}N_2O_4 \cdot HCl \cdot H_2O$ Theory: C, 63.79; H, 8.98; N, 5.31 Found: C, 63.54; H, 8.93; N, 4.94

EXAMPLE 17

N-Ethyl-N'-2-(D-(1-(trans-4-(3-hydroxyphenyl)-3,4-dimethyl-1-piperidinyl)-3-phenyl)propyl)urea hydrochloride monohydrate (DIASTEREOMER B). [Q-$CH_2$-$CH[CH_2(C_6H_5)]$-$NHC(O)NHCH_2CH_3 \cdot HCl \cdot H_2O$].

To a solution of 300 mg (0.9 mMol) D-(−)-1-(trans-4-(3-hydroxyphenyl)-3,4-dimethyl-1-piperidinyl)-3-phenyl-2-aminopropane [Diastereomer B from Preparation IX] in dichloromethane (20 ml) at 0° C. was added a solution of 128 mg (1.8 mMol) ethyl isocyanate in dichloromethane (10 ml) dropwise. The reaction mixture was then stirred for 1 hour at room temperature. The volatiles were then concentrated under reduced pressure and the residue dissolved in 1:1 methanol:25% aqueous sodium hydroxide. The resulting solution was stirred for 1 hour at room temperature and the solution concentrated to half volume under reduced pressure. The remaining solution was adjusted to pH = 9.8 with hydrochloric acid and the resulting mixture extracted with ethyl acetate. The organic extracts were combined, washed with water, dried over potassium carbonate and concentrated under reduced pressure. The resulting residue was purified by silica gel chromatography, eluting with ethyl acetate. Fractions containing product were combined, concentrated under reduced pressure and the residue converted to the hydrochloride salt. The title compound was recovered as a colorless solid (300 mg, 71.8%).

m.p = 120°–124° C.

ms (fd) = 409(M+ − 1), 410(M+)

$[\alpha]_{365}(CH_3OH) = -134.56°$

Calculated for $C_{25}H_{35}N_3O_2 \cdot HCl \cdot H_2O$: Theory: C, 64.70; H, 8.24; N, 9.05 Found: C. 65.03 H, 8.27: N, 8.91

EXAMPLE 18

Trans-(4-((1-((4-(3-hydroxyphenyl)-3,4-dimethyl-1-piperidinyl)methyl)-2-phenylethyl)amino)-4-oxobutyl) carbamic acid, 1,1 dimethylethyl ester monohydrochloride. [Q-$CH_2CH[CH_2(C_6H_5)]NHC(O)(CH_2)_3NH$-$C(O)OC(CH_3)_3 \cdot HCl$].

A solution of 507 mg (1.5 mMol) DL-1-(trans-4-(3-hydroxyphenyl)-3,4-dimethyl-1-piperidinyl)-3-phenyl-2-aminopropane [Preparation VIII] and 305 mg (1.5 mMol) N-tBOC-4-aminobutanoic acid in dimethylformamide (50 ml) were contacted as described in Example 2. The title compound was recovered as a mixture of diastereomeric pairs (400 mg, 47.6%).

m.p. = 107°–110° C. (with decomposition)

ms (fd) = 523(M+ − 1), 524(M+)

Calculated for $C_{31}H_{45}N_3O_4 \cdot HCl$: Theory: C, 66.47; H, 8.28; N, 7.50 Found: C, 66.27; H, 8.31; N, 7.66

EXAMPLE 19

4-((2-(Trans-4-(3-hydroxyphenyl)-3,4-dimethyl-1-piperidinyl)ethyl)phenylamino-4-oxobutanoic acid monohydrate. [Q-$(CH_2)_2N(C_6H_5)C(O)(CH_2)_2$-$C(O)OH \cdot H_2O$].

A 1.5 gm (4.63 mMol) portion of N-phenyl-2-(trans-4-(3-hydroxyphenyl)-3,4-dimethyl-1-piperidinyl)-ethylamine [Preparation XVI] was contacted with succinic anhydride (465 mg) and triethylamine (935 mg) in 100 ml dry THF and stirred for 48 hours. The solvent was removed and the residue passed over a silica column eluting with methanol ethyl acetate (1:9). After solvent was removed from the fraction containing product, the resulting solid was slurried in hexane and filtered to provide 814 mg of solid product.

m.p. = 90°–100° C.

Calculated for $C_{25}H_{32}N_2O_4 \cdot H_2O$: Theory: C, 67.85; H, 7.74; N, 6.33 Found: C, 67.61; H, 7.60; N, 6.06

EXAMPLE 20

Trans-5-(phenyl-(2-(4-(3-hydroxyphenyl)-3,4-dimethyl-1-piperidinyl)ethyl)amino)-5-oxopentanoic acid monohydrate. [Q-(CH$_2$)$_2$N(C$_6$H$_5$)C(O)(CH$_2$)$_3$-C(O)OH.H$_2$O].

A 500 mg (1.54 mMol) portion of N-phenyl-2-(trans-4-(3-hydroxyphenyl)-3,4-dimethyl-1-piperidinyl)-ethylamine [Preparation XVI] was contacted with glutaric anhydride (176 mg) under the conditions described in Example 19. The title compound was recovered as a colorless solid (260 mg, 37.9%).

m.p.=60°-75° C.

Calculated for C$_{26}$H$_{34}$N$_2$O$_4$.H$_2$O: Theory: C, 68.40; H, 7.95; N, 6.14 Found: C, 68.55; H, 7.97; N, 5.92

EXAMPLE 21

3-(cyclohexyl-(2-(trans-4-(3-hydroxyphenyl)-3,4-dimethyl-1-piperidinyl)ethyl)amino)-3-oxopropanoic acid monohydrate. [Q-(CH$_2$)$_2$N(C$_6$H$_{11}$)C(O)CH$_2$-C(O)OH.H$_2$O].

A 1 mMol portion of N-cyclohexyl-2-(trans-4-(3-hydroxyphenyl)-3,4-dimethyl-1-piperidinyl)ethylamine [Preparation XII] was treated with ethyl malonoyl chloride according to the procedure of Example 10. The resulting ester was hydrolyzed according to the procedure of Example 13 to give the title compound as a colorless solid (185 mg, 42.6%).

m.p.=131°-135° C.

ms (fd)=417(M$^+$), 418(M$^+$+1)

Calculated for C$_{24}$H$_{38}$N$_2$O$_5$: Theory: C, 66.33; H, 8.81; N, 6.45 Found: C, 66.53; H, 8.68; N, 6.21

EXAMPLE 22

4-(Cyclohexyl-(2-(trans-4-(3-hydroxyphenyl)-3,4-dimethyl-1-piperidinyl)ethyl)amino)-4-oxobutanoic acid monohydrate. Q-(CH$_2$)$_2$N(C$_6$H$_{11}$)C(O)(CH$_2$)$_2$-C(O)OH.H$_2$O].

A 500 mg (1.5 mMol) portion of N-cyclohexyl-2-(trans-4-(3-hydroxyphenyl)-3,4-dimethyl-1-piperidinyl)-ethylamine [Preparation XII] was treated with succinic anhydride according to the procedure described in Example 1. The title compound was recovered by recrystallization from ethyl acetate as a colorless, crystalline solid (200 mg, 29.7%)

m.p=111.5°-113° C.

ms (fd)=430(M$^-$)

Calculated for C$_{25}$H$_{38}$N$_2$O$_4$H$_2$O: Theory: C, 66.87; H, 8.90; N, 6.24 Found: C, 66.71; H, 8.71; N, 6.10

EXAMPLE 23

5-(Cyclohexyl-(2-(trans-4-(3-hydroxyphenyl)-3,4-dimethyl-1-piperidinyl)ethyl)amino)-5-oxopentanoic acid monohydrate. [Q-(CH$_2$)$_2$N(C$_6$H$_{11}$)C(O)(CH$_2$)$_3$-C(O)OH.H$_2$O].

A 400 mg (1.2 mMol) portion of N-cyclohexyl-2-(trans-4-(3-hydroxyphenyl)-3,4-dimethyl-1-piperidinyl)-ethylamine [Preparation XII] was contacted with glutaric anhydride (150 mg) in DMF (50 ml) with stirring at room temperature for 24 hours. The mixture was stripped to dryness and the solid triturated in ethyl ether. The solid was passed through a silica column using ethyl acetate methanol (4:1). The recovered solid was slurried in hot ethyl acetate three times, filtered, the filtrate stripped to dryness and triturated with ethyl ether to provide the title compound as a colorless solid (173 mg, 31.2%)

m.p.=110° C. (foam)

Calculated for C$_{26}$H$_{40}$N$_2$O$_4$.H$_2$O: Theory: C, 67.50; H, 9.08; N, 6.06 Found: C, 67.76; H, 8.95; N, 6.00

EXAMPLE 24

4-(cyclopentyl-2-(trans-4-(3-hydroxyphenyl)-3,4-dimethyl-1-piperidinyl)ethyl)amino)-4-oxobutanoic acid hemihydrate. [Q-(CH$_2$)$_2$N(C$_5$H$_9$)C(O)(CH$_2$)$_2$-C(O)OH.½H$_2$O].

A 600 mg (1.9 mMol) portion of N-cyclopentyl-2-(trans-4-(3-hydroxyphenyl)-3,4-dimethyl-1-piperidinyl)-ethylamine [Preparation XIII] was treated with succinic anhydride according to the procedure described in Example 1. The title compound was recrystallized from ml acetonitrile/0.5 ml H$_2$O to provide 320 mg of colorless solid.

m.p.=128° C.

ms (fd)=417 (M$^+$+1)

Analysis for C$_{24}$H$_{36}$N$_2$O$_4$.½H$_2$O Theory: C, 67.72; H, 8.78; N, 6.58 Found: C, 67.75; H, 8.90; N, 6.57

EXAMPLE 25

5-(cyclohexyl-(3-(trans-4-(3-hydroxyphenyl)-3,4-dimethyl-1-piperidinyl)propyl)amino)-5-oxopentanoic acid. [Q-(CH$_2$)$_3$N(C$_6$H$_{11}$)C(O)(CH$_2$)$_3$-C(O)OH].

A 500 mg (1.45 mMol) portion of N-cyclohexyl-3-(trans-4-(3-hydroxyphenyl)-3,4-dimethyl-1-piperidinyl)-propylamine [Preparation XIV] was contacted with glutaric anhydride (165 mg) in dimethylformamide (50 ml) and refluxed for 1 hour. The solvent removed and the residue passed through a silica column eluting with methanol. The solvent was removed, the residue was dissolved in hot ethyl acetate, the solution filtered, and the solvent removed. The solid was recrystallized from ethyl acetate hexane to provide the title compound as a colorless, crystalline solid (380 mg, 57.1%)

m.p.=100°-108° C.

Calculated for C$_{27}$H$_{42}$N$_2$O$_4$: Theory: C, 70.71; H, 9.23; N, 6.11 Found: C, 70.42; H, 9.03; N, 6.41

EXAMPLE 26

4-(cyclohexylmethyl-(2-(trans-4-(3-hydroxyphenyl)-3,4-dimethyl-1-piperidinyl)ethyl)amino)-4-oxobutanoic acid monohydrate. [Q-(CH$_2$)$_2$N[CH$_2$(C$_6$H$_{11}$)]C(O)(CH$_2$)$_2$C(O)OH.H$_2$O].

A 280 mg (0.82 mMol) portion of N-cyclohexylmethyl-2-(trans-4-(3-hydroxyphenyl)-3,4-dimethyl-1-piperidinyl)ethylamine [Preparation XVIII] was treated with succinic anhydride (82 mg) according to the procedure described in Example 5. The product was purified by passing through a silica column eluting with a solvent gradient of ethyl acetate to ethyl acetate methanol (1:1). The title compound was recovered as a colorless solid (240 mg, 63.2%)

m.p.=70°-73° C.

ms (fd)=444(M$^+$), 445(M$^+$+1)

Calculated for C$_{26}$H$_{40}$N$_2$O$_4$: Theory: C, 67.44; H, 9.15; N, 6.06 Found: C, 67.16; H, 8.88; N, 5.89

EXAMPLE 27

Trans-5-(cyclohexylmethyl(3-(4-(3-hydroxyphenyl)-3,4-dimethyl-1-piperidinyl)propyl)amino)-5-oxopentanoic acid monohydrate. [Q-(CH$_2$)$_3$N[CH$_2$(C$_6$H$_{11}$)]C(O)(CH$_2$)$_3$-C(O)OH.H$_2$O].

A 520 mg (1.45 mMol) portion of N-cyclohexylmethyl-3-(trans-4-(3-hydroxyphenyl)-3,4-dimethyl-1-piperidinyl)propylamine [Preparation XIX] was treated with glutaric anhydride (166 mg) in dimethylformamide (50 ml) according to the procedure described in Example 5 with the final mixture heated for 5 minutes with a heat gun. The product was purified by passing through a silica column eluting with a solvent gradient of ethyl acetate-methanol (9:1) to methanol. The title compound was recovered as a colorless solid (510 mg, 71.7%)

m.p. = 102°–105° C.

ms (fd) = 472(M+), 473(M+ +1)

Calculated for $C_{28}H_{44}N_2O_4.H_2O$: Theory: C, 68.57; H, 9.38; N, 5.71 Found: C, 68.47; H, 9.04; N, 5.98

EXAMPLE 28

4-(3-methylbutyl-(2-(trans-4-(3-hydroxyphenyl)-3,4-dimethyl-1-piperidinyl)ethyl)amino)-4-oxobutanoic acid monohydrate. [Q-$(CH_2)_2N[(CH_2)_2CH(CH_3)_2]C(O)-(CH_2)_2C(O)OH.H_2O$].

A 400 mg (1.26 mMol) portion of 3-methylbutyl-(2-(trans-4-(3-hydroxyphenyl)-3,4-dimethyl-1-piperidinyl)-ethylamine [Preparation XX] was treated with succinic anhydride (126 mg) in dimethylformamide (40 ml) according to the procedure described in Example 27. Purification was with column chromatography eluting with ethyl acetate to methanol solvent gradient. The title compound was recovered as a colorless solid (490 mg, 89.1%).

m.p. = 83°–86° C.

ms (fd) = 418(M+), 419(M+ +1)

Calculated for $C_{24}H_{38}N_2O_4.H_2O$: Theory: C, 65.96; H, 9.16; N, 6.41 Found: C, 66.20; H, 9.09; N, 6.36

EXAMPLE 29

5-(2-Methylpropyl-(3-(trans-4-(3-hydroxyphenyl)-3,4-dimethyl-1-piperidinyl)propyl)amino)-5-oxopentanoic acid monohydrate. [Q-$(CH_2)_3$-$N[CH_2CH(CH_3)_2]C(O)(CH_2)_3$-$C(O)OH.H_2O$]

A 340 mq (1.07 mMol) portion of 2-methylpropyl(3-(4-(3-hydroxyphenyl)-3,4-dimethyl-1-piperidinyl)-propylamine [Preparation XXI] was treated with glutaric anhydride (122 mg) in dimethylformamide (50 ml) according to the procedure described in Example 27. The title compound was recovered as a colorless solid (360 mg, 74.6%).

m.p. = 66°–70° C.

Calculated for $C_{25}H_{40}N_2O_4.H_2O$: Theory: C, 66.30; H, 9.32; N, 6.22 Found: C, 66.38; H, 9.10; N, 6.10

Example 30

4-(Cyclohexyl-(2-(trans-4-(3-hydroxyphenyl)-3,4-dimethyl-1-piperidinyl)ethyl)amino)-4-oxobutanoic acid 1-methyl-ethyl ester. [Q-$(CH_2)_2$-$N(C_6H_{11})C(O)(CH_2)_2C(O)OCH(CH_3)_2$].

To a solution of 500 mg (1.51 mMol) of 4-(cyclohexyl-(2-(trans-4-(3-hydroxyphenyl)-3,4-dimethyl-1-piperidinyl)ethylamine [Preparation XII] in DMF (45 ml) were added sequentially 242 mg (1.51 mMol) monoisopropyl succinate, 204 mg (1.51 mMol) 1-hydroxybenzotriazole and 311 mg (1.51 mMol) dicyclohexylcarbodiimide. The reaction mixture was allowed to stir for 48 hours at room temperature under nitrogen. The reaction mixture was then cooled to 0° C., filtered and the filter cake washed with cold dimethylformamide. The filtrate was concentrated under reduced pressure and the residue diluted with water. The pH of this solution was adjusted to 9.8 with 1N NaOH and the mixture was extracted well with butanol toluene (3:1). The organic extracts were combined, washed with water, dried over potassium carbonate and concentrated under reduced pressure. The residue was purified by silica gel chromatography, eluting with ethyl acetate. The title compound was isolated as a colorless foam (450 mg, 63%).

m.p. = 55°–60° C.

Calculated for $C_{28}H_{45}N_2O_4$: Theory: C, 71.00; H, 9.58; N, 5.91 Found: C, 71.08; H, 9.36; N, 5.89

EXAMPLE 31

4-(Cyclohexyl-(2-(trans-4-(3-hydroxyphenyl)-3,4-dimethyl-1-piperidinyl)ethyl)amino)-4-oxobutanoic acid propyl ester. Q-$(CH_2)_2N(C_6H_{11})C(O)(CH_2)_2$-$C(O)O(CH_2)_2CH_3$].

A 500 mg (1.51 mMol) portion of cyclohexyl-2-(trans-4-(3-hydroxyphenyl)-3,4-dimethyl-1-piperidinyl)ethylamine [Preparation XII] was contacted with monopropyl succinate (242 mg), HOBT (204 mg), DCC (311 mg) and DMF (45 ml) under the conditions described in Example 30. The title compound (317 mg) was isolated as a white foam.

m.p. = 50°–60° C.

ms (fd) = 473 M+

Calculated for $C_{28}H_{44}N_2O_4$: Theory: C, 71.15; H, 9.38; N, 5.93 Found: C, 70.87; H, 9.22; N, 5.98

EXAMPLE 32

5-(Cyclohexyl-(2-(trans-4-(3-hydroxyphenyl)-3,4-dimethyl-1-piperidinyl)ethyl)amino)-5-oxopentanoic acid ethyl ester monohydrochloride. [Q-$(CH_2)_2N(C_6H_{11})C(O)-(CH_2)_3C(O)OCH_2CH_3.HCl$].

A 575 mg (1.74 mMol) portion of N-cyclohexyl-2-(trans-4-(3-hydroxyphenyl)-3,4-dimethyl-1-piperidinyl)ethylamine [Preparation XII] was contacted with monoethyl glutarate (278 mg), HOBT (235 mg) and DCC (360 mg) in DMF (50 ml) under the conditions described in Example 30. The title compound was isolated as its hydrochloride salt to give 400 mg (45.1%) of a colorless solid.

m.p. = 90°–110° C.

Calculated for $C_{28}H_{44}N_2O_4.HCl$: Theory: C, 66.06; H, 8.91; N, 5.50 Found: C, 65.85; H, 9.15; N, 5.61

EXAMPLE 33

5-(Cyclohexyl-(3-(trans-4-(3-hydroxyphenyl)-3,4-dimethyl-1-piperidinyl)propyl)amino)-5-oxopentanoic acid ethyl ester monohydrochloride. [Q-$(CH_2)_3N(C_6H_{11})C(O)-(CH_2)_3C(O)OCH_2CH_3.HCl$].

A 600 mg (1.74 mMol) portion of N-cyclohexyl-3-(trans-4-(3-hydroxyphenyl)-3,4-dimethyl-1-piperidinyl)propylamine [Preparation XIV] was contacted with monoethyl glutarate (278 mg), HOBT (235 mg) and DCC (360 mg) in DMF (50 ml) under the conditions described in Example 30. The title compound was isolated as its hydrochloride salt to give 160 mg (17.6%) of a colorless solid.

m.p. = 75°–85° C. (foam)

Calculated for $C_{29}H_{46}N_2O_4.HCl$: Theory: C, 66.58; H, 9.06; N, 5.35 Found: C, 66.64; H, 8.82; N, 5.16

EXAMPLE 34

N-Cyclohexyl-N-(2-(trans-4-(3-hydroxyphenyl)-3,4-dimethyl-1-piperidinyl)ethyl)propanediamidehydrochloride monohydrate. [Q-$(CH_2)_2N(C_6H_{11})C(O)CH_2C(O)NH_2$].

A portion of N-cyclohexyl-2-(trans-4-(3-hydroxyphenyl)-3,4-dimethyl-1-piperidinyl)ethylamine [Preparation XII] was contacted with ethyl malonoyl chloride as described in Example 10 to give 500 mg (1.02 mMol) 3-(cyclohexyl-(2-(trans-4-(3-hydroxyphenyl)-3,4-dimethyl-1-piperidinyl)ethyl)amino)-3-oxopropionic acid ethyl ester hydrochloride. This material was stirred overnight at room temperature in 10 ml of ammonium hydroxide (28%). The mixture was evaporated to dryness. The residue was partitioned between butanoltoluene (3:1) and water with the pH of the water layer adjusted to 9.8 with 1N sodium hydroxide. The organic layer was separated, dried over potassium carbonate, and the solvent evaporated. The residue was passed through a silica column eluting with an ethyl acetate to ethyl acetate-methanol (1:1) gradient. The solvent was removed to provide 290 mg of the free base compound.

ms (fd)=415 (M+), 416 (M++1)

The free base was converted to the HCl salt and dried to provide the title compound as a colorless solid (213 mg, 44.4%).

m.p.=113°-118° C.

Calculated for $C_{24}H_{37}N_3O_3.HCl.H_2O$: Theory: C, 61.32; H, 8.58; N, 8.94 Found: C, 61.32; H, 8.37; N, 8.66

EXAMPLE 35

N-Cyclohexyl-N-(2-(trans-4-(3-hydroxyphenyl)-3,4-dimethyl-1-piperidinyl)ethyl)butanediamide monohydrochloride. [Q-$(CH_2)_2N(C_6H_{11})C(O)(CH_2)_2$-$C(O)NH_2.HCl$].

A 500 mg (1.51 mMol) portion of N-cyclohexyl-2-(trans-4-(3-hydroxyphenyl)-3,4-dimethyl-1-piperidinyl)-ethylamine [Preparation XII] was contacted with succinamic acid (177 mg), HOBT (204 mg) and DCC (312 mg) in DMF (50 ml) under the conditions described in Example 30 to give the free base of the title compound as a colorless, crystalline solid (200 mg, 30.8%).

m.p.=85°-100° C. (foam)

ms (fd)=430(M+)

Calculated for $C_{25}H_{39}N_3O_3$: Theory: C, 69.90; H, 9.15; N, 9.78 Found: C, 69.82; H, 9.01; N, 9.66

The hydrochloride salt of the above free base was formed to give the title compound as a colorless solid.

m.p.=160°-162° C.

EXAMPLE 36

N-Methyl-3-oxo-3-((2-(trans-4-(3-hydroxyphenyl)-3,4-dimethyl-1-piperidinyl)ethyl)cyclohexylamino)-propanamidemonohydrochloride monohydrate. [Q-$(CH_2)_2N(C_6H_{11})C(O)$-$CH_2C(O)NHCH_3.HCl.H_2O$].

A 500 mg (1.02 mMol) portion of Q-$(CH_2)_2N(C_6H_{11})C(O)CH_2C(O)OCH_2CH_3.HCl$ was contacted with methylamine (25 ml, 40%) under the reaction conditions described in Example 34 except the mixture was stirred for 2 hours. The product was purified through a silica column using ethyl acetate to ethyl acetate-methanol (1:1) solvent gradient. The free base was recovered (270 mg).

ms (fd)=429(M+-1), 430(M+)

The free base was converted to the HCl salt and dried to gain the title compound (277 mg).

m.p.=82°-85° C. (foam)

Calculated for $C_{25}H_{39}N_3O_3.HCl.H_2O$: Theory: C, 62.03; H, 8.75; N, 8.68 Found: C, 61.84; H, 8.54; N, 8.48

EXAMPLE 37

N-(3-(trans-4-(3-hydroxyphenyl)-3,4-dimethyl-1-piperidinyl)propyl)-N-cyclohexylpentanediamide monohydrochloride monohydrate. [Q-$(CH_2)_3N(C_6H_{11})C(O)(CH_2)_3$-$C(O)NH_2.HCl.H_2O$.

A 688 mg (2.00 mMol) portion of N-cyclohexyl-3-(trans-4-(3-hydroxyphenyl)-3,4-dimethyl-1-piperidinyl)-propylamine [Preparation XIV] was contacted with glutaramic acid (262 mg), HOBT (270 mg) and DCC (412 mg) in DMF (50 ml) under the conditions described in Example 30. The solid product was converted to the HCl salt to give the title compound as a colorless solid (290 mg, 28.3%).

m.p.=81°-84° C.

Calculated for $C_{27}H_{43}N_3O_3.HCl.H_2O$: Theory: C, 63.25; H, 8.98; N, 8.20 Found: C, 62.94; H, 8.79; N, 7.99

EXAMPLE 38

N-cyclohexyl-N-(2-(trans-4-(3-hydroxyphenyl)-3,4-dimethyl-1-piperidinyl)ethyl)-N'-(2-(methylamino)-2-oxoethyl)propanediamide monohydrochloride. [Q-$(CH_2)_2N(C_6H_{11})C(O)CH_2C(O)NHCH_2$-$C(O)NHCH_3.HCl$].

A 1.05 gm (2.5 mMol) portion of 4-(cyclohexyl(2-(trans-4-(3-hydroxyphenyl)-3,4-dimethyl-1-piperidinyl)ethyl)amino)-4-oxobutanoic acid was contacted with glycine ethyl ester hydrochloride under the conditions described in Example 30 to give N-cyclohexyl-N-(2-(trans-4-(3-hydroxyphenyl)-3,4-dimethyl-1-piperidinyl)ethyl)-N'-(2-ethyl acetyl)propanediamide hydrochloride (950 mg).

m.p.=110°-114° C.

Calculated for $C_{27}H_{42}N_3O_5.HCl$: Theory: C, 62.S0; H, 8.24; N, 7.80 Found: C, 62.76; H, 8.32' N, 7.95

A 350 mg (0.65 mMol) portion of this material was then subjected to the reaction conditions described in Example 36 with dioxane and under nitrogen to give the title compound as a colorless solid (145 mg, 42.6%).

m.p.=124°-128° C.

Calculated for $C_{27}H_{42}N_4O_4.HCl$: Theory: C, 61.99; H, 8.28; N, 10.71 Found: C, 62.10; H, 8.36; N, 10.65

EXAMPLE 39

N-(1,4-dioxo-4-((2-(4-(3-hydroxyphenyl)-3,4-dimethyl-1piperidinyl)ethyl)phenylamino)butyl)leucine monohydrochloride monohydrate. [Q-$(CH_2)_2N(C_6H_5)C(O)(CH_2)_2C(O)NHCH$-$[CH_2CH(CH_3)_2]C(O)OH.HCl.H_2O$].

A 1.06 gm (2.4 mMol) portion of 4-((2-(trans-4-(3-hydroxyphenyl)-3,4-dimethyl-1-piperidinyl)ethyl)-phenylamino-4-oxobutanoic acid was reacted with L-leucine methyl ester hydrochloride under the conditions described in Example 30 to give N-(1,4-dioxo-4-((2-(trans-4-(3-hydroxyphenyl)-3,4-dimethyl-1-piperidinyl)-ethyl)phenylamino)butyl)leucine methyl ester as a crystalline solid (660 mg, 49.9%).

m.p.=60°-65° C.

Calculated for $C_{32}H_{45}N_3O_5$: Theory: C, 69.66; H, 8.22; N, 7.61 Found: C, 69.45; H, 8.45; N, 7.62

A 340 mg (0.62 mMol) portion of this material was then dissolved in dioxane (30 ml) and 6N hydrochloric acid (20 ml) and the resulting solution stirred at reflux for 3 hours. The reaction mixture was then concentrated under reduced pressure and the residue triturated with diethyl ether to give the title compound as a colorless solid (280 mg).

m.p.=100°-115° C. (foam)

Calculated for $C_{31}H_{43}N_3O_5.HCl.H_2O$: Theory: C, 62.87; H, 7.83; N, 7.10 Found: C, 62.57; H, 7.74; N, 6.93

EXAMPLE 40

N-cyclohexyl-N-(2-(trans-4-(3-hydroxyphenyl)-3,4-dimethyl-1-piperidinyl)ethyl)-N'-(2-methyl-4-oxobutyl)-1-oxo-1,4-butanediamine hydrochloride. [Q-(CH$_2$)$_2$N(C$_6$H$_{11}$)-C(O)(CH$_2$)$_3$NH-C(O)CH$_2$CH(CH$_3$)$_2$.HCl].

To a solution of 20 gm (194 mMol) 4-aminobutyric acid in dichloromethane (700 ml) was added 56.8 ml (407 mMol) triethylamine and the mixture was stirred for 10 minutes. To the reaction mixture was then added a solution of 47.4 ml (388 mMol) isovaleryl chloride in dichloromethane (200 ml) dropwise and the resulting mixture was then stirred at room temperature for 2 hours. The reaction mixture was then filtered and the volatiles removed under reduced pressure. The residue was dissolved in 1N aqueous sodium hydroxide (150 ml) and the solution was stirred for 1.5 hours at room temperature. The aqueous solution was extracted with diethyl ether and the combined ether extracts were washed with water. All aqueous phases were combined and then acidified with concentrated hydrochloric acid. This mixture was then extracted well with ethyl acetate. These organic extracts were combined, dried over magnesium sulfate and concentrated under reduced pressure. The residue was slurried in hexane and the hexane decanted from the residue. Remaining residue was distilled in a bulb to bulb apparatus at 220° C. at 0.05 mmHg to give 8.0 g (22%) N-isovaleryl-4-aminobutyric acid.

Calculated for C$_9$H$_{17}$NO$_3$: Theory: C, 57.73; H, 9.15; N, 7.48 Found: C, 57.67; H, 9.21; N, 7.25

A 500 mg (1.5 mMol) portion of N-cyclohexyl-2-(trans-4-(3-hydroxyphenyl)-3,4-dimethyl-1-piperidinyl)-ethylamine [Preparation XII] was contacted with N-isovaleryl-4-aminobutanoic acid (283 mg), HOBT (204 mg) and DCC (312 mg) in DMF (50 ml) under the conditions described in Example 32 to give the title compound as a colorless solid (262 mg, 32.6%).

m.p. = 100°-115° C.

Calculated for C$_{30}$H$_{49}$N$_3$O$_3$.HCl: Theory: C, 67.20; H, 9.40; N, 7.84 Found: C, 67.03; H, 9.34; N, 7.90

EXAMPLE 41

2-((1,4-dioxo-4-(cyclohexyl-(2-(trans-4-(3-hydroxyphenyl)-3,4-dimethyl-1-piperidinyl)ethyl)amino)-butyl)-amino)-3-phenylpropanoic acid, methyl ester. [Q(CH$_2$)$_2$N(C$_6$H$_{11}$)C(O)(CH$_2$)$_2$-C(O)NHCH[CH$_2$(C$_6$H$_5$)]C(O)OCH$_3$].

A 1.08 gm (3.0 mMol) portion of N-cyclohexyl-2-(trans-4-(3-hydroxyphenyl)-3,4-dimethyl-1-piperidinyl)-ethylamine [Preparation XII] was contacted with L-phenylalanine methyl ester hydrochloride (541 mg), HOBT (340 mg), diethylamine (0.44 ml), and DCC (518 mg) in DMF (100 ml) under the conditions described in Example 32 to give the title compound as a colorless solid (800 mg).

m.p. = 60°-90° C.

[α]$_{589}$ = +3.37
[α]$_{365}$ = +21.39

Calculated for C$_{35}$H$_{49}$N$_3$O$_5$: Theory: C, 71.05; H, 8.35; N, 7.10 Found: C, 70.98; H, 8.46; N, 7.20

EXAMPLE 42

N-(2-(trans-4-(3-hydroxyphenyl)-3,4-dimethyl-1-piperidinyl)ethyl)-2-(acetylamino)-5-((imino(nitroamino)-methyl)amino)pentanamide monohydrate. [Q-(CH$_2$)$_2$-NHC(O)CH[NH-C(O)CH$_3$](CH$_2$)$_3$NHC(NH)NHNO$_2$.H$_2$O].

To a solution of 2.0 gm (8.9 mMol) arginine methyl ester hydrochloride and 1.5 gm (14.8 mMol) triethylamine in dimethylformamide (150 ml) was added 776 mg (7.4 mMol) acetic anhydride dropwise at 0° C. The reaction mixture was stirred at room temperature for 1 hour and then the volatiles removed under reduced pressure. The residue was purified using silica gel chromatography, eluting with ethyl acetate containing 0-50% methanol, to give N-acetyl arginine methyl ester as a crystalline solid (2.53 g).

m.p. = 145°-146.5° C.

Calculated for C$_9$H$_{17}$N$_5$O$_5$: Theory: C, 39.27; H, 6.23; N, 25.44 Found: C, 38.98; H, 6.19; N, 25.69

To a solution of 1.65 gm (6 mMol) of this methyl ester in methanol (48 ml) and water (98 ml) was added 0.5 N aqueous sodium hydroxide (12.45 ml) and the reaction mixture was then stirred at room temperature for 2 hours. The methanol was then removed under reduced pressure and the remaining solution diluted with water. The solution was then extracted once with ethyl acetate. The remaining aqueous phase was then made acidic with 1N hydrochloric acid and extracted with 3:1 butanol:toluene. These organic extracts were combined, washed with saturated aqueous sodium chloride, dried over magnesium sulfate and concentrated under reduced pressure to give N-acetyl arginine.

The material thus prepared was reacted with a 400 mg (1.6 mMol) portion of 2-(trans-4-(3-hydroxyphenyl)3,4-dimethyl-1-piperidinyl)ethylamine [Preparation XII] HOBT (216 mg) and DCC (330 mg) in DMF (50 ml) under the conditions described in Example 30 to give the title compound as a colorless solid (360 mg).

m.p. = 62°-65° C. [α]$_{365}$ = −32.28°

Calculated for C$_{23}$H$_{39}$N$_7$O$_6$.H$_2$O: Theory: C, 54.11; H, 7.64; N, 19.21 Found: C, 54.12; H, 7.34; N, 18.92

EXAMPLE 43

Trans-N-(2-(4-(3-hydroxyphenyl)-3,4-dimethyl-1-piperidinyl)ethyl)-2-((3-methyl-1-oxobutyl)amino)-5-((imino(nitroamino)methyl)amino) pentanamide. [Q-(CH$_2$)$_2$NHC(O)-CH[NHC(O)CH$_2$CH(CH$_3$)$_2$](CH$_2$)$_3$NHC(NH)NHNO$_2$].

A 2.0 g (8.9 mMol) portion of arginine methyl ester hydrochloride was contacted with isovaleric acid (755 mg), HOBT (1 g), triethylamine (747 mg) and DCC (1.52 g) in DMF (150 ml) under the conditions described in Example 30 to give N-isovaleryl-arginine methyl ester as a crystalline solid (1.71 g).

m.p. = 133°-135° C.

Calculated for C$_{12}$H$_{23}$N$_5$O$_5$: Theory: C, 45.42; H, 7.31; N, 22.07 Found: C, 45.71; H, 7.55; N, 22.31

The N-isovaleryl arginine methyl ester thus prepared was converted to its corresponding acid and then coupled with a 317 mg (1.3 mMol) portion of 2-(trans-4-(3-hydroxyphenyl)-3,4-dimethyl-1-piperidinyl)-ethylamine [Preparation XII] under the conditions described in Example 30 using HOBT (173 mg) and DCC (264 mg) in DMF (30 ml) to give the title compound as a colorless solid (400 mg).

m.p. = 182°-184° C. (with decomposition)

Calculated for C$_{26}$H$_{43}$N$_7$O$_5$: Theory: C, S8.52; H, 8.12; N, 18.37 Found: C, 58.43; H, 8.21; N, 18.14

EXAMPLE 44

(1-(((2-(Trans-4-(3-hydroxyphenyl)-3,4-dimethyl-1-piperidinyl) ethyl)amino)carbonyl)-4-((imino(nitroamino)methyl)amino)butyl) carbamic acid, 1,1-dimethylethyl ester. [Q-(CH$_2$)$_2$NHC(O)CH[NH-C(O)OC(CH$_3$)$_3$](CH$_2$)$_3$-NHC(NH)NHNO$_2$]. N-tBOC-nitro-L-arginine (798 mg) 2-[Trans-4-(3-hydroxyphenyl)-3,4-dimethyl-1-piperidinyl]ethylamine (620 mg), HOBT (338 mg), DCC (516 mg), and DMF (50 ml). The procedure of Example 43 was followed with these reagents to give the title compound as a colorless solid (870 mg).

m.p. = 107°-115° C.

Calculated for C$_{26}$H$_{43}$N$_7$O$_6$: Theory: C, 56.81; H, 7.89; N, 17.84 Found: C, 57.00; H, 7.93; N, 17.65

EXAMPLE 45

Preparation of (3R,4R)-(S)-Q-CH$_2$-C(E)H-NHC(O)-(CH$_2$)$_3$CO$_2$H where E is cyclohexylmethyl.

A. (+)-(3R,4R)-dimethyl-4-(3-hydroxyphenyl)-piperidine (Q-H) (5 g) prepared as in Preparation I, (L)-HOOC-C(R)H-NH.tBOC (6.55 g), HOBT (3.30 g), DCC (5.02 g) were dissolved in dry DMF (800 ml) and stirred three days at room temperature under nitrogen. The mixture was evaporated to dryness and the residue taken into ethyl acetate. The solution was washed one time with water, dried over K$_2$CO$_3$ and the solvent evaporated to provide 21.38 g of product. This material was passed over a silica column eluting with a solvent gradient of hexane-ethyl acetate (9:1) to ethyl acetate. Evaporation of solvent provided 11.01 g of the product.

[α]$_{365}$(CH$_3$OH) = +126.37° ms (fd) = 458 (M+)

Analysis for C$_{27}$H$_{42}$N$_2$O$_4$ Theory C, 70.71; H, 9.23; N, 6.11 Found C, 70.52; H, 9.14; N, 5.97

B. Preparation of (3R,4R)-(S)-Q-C(O)-C(E)H-NH$_2$

Product from 45 A above (11 g), 6N HCl (600 ml), and methanol (300 ml) were mixed together and stirred overnight at room temperature. The mixture was then evaporated to dryness and the residue partitioned between water (1 L) and a solution of butanol-toluene (3:1, 1 L). The pH was adjusted to 9.8 using 1N NaOH and the layers were separated. The organic layer was washed one time with water, dried over K$_2$CO$_3$ and evaporated to provide 9.84 g of a viscous yellow oil. This material was passed over a silica column using a solvent gradient of ethyl acetate-methanol (9:1) to ethyl acetate-methanol (1:1) to provide 6.13 g of product.

ms (fd) = 359 (M$^+$+1)

[α]$_{365}$ = +104.30°

C. Preparation of (3R,4R)-(S)Q-CH$_2$CH(E)-NH$_2$

Product from 45 B above (6.1 g) in toluene (160 ml) was added dropwise to RedAl (22 ml) at room temperature under nitrogen. The mixture was then heated at 75°-80° C. for 5 hours and then cooled to room temperature. The mixture was added to a pH 10 buffer (300 ml) and then the pH was adjusted to 9.8 with 1N HCl. This mixture was extracted with a butanol-toluene (3:1) solution. The organic layer was separated, washed one time with water and dried over K$_2$CO$_3$. Evaporation of the solvent provided 5.87 g of a tan solid. This was passed over a silica column eluting with a solvent gradient of ethyl acetate-methanol (9:1) to ethyl acetate-methanol (1:1). The evaporation of solvent provided 4.91 g of a white crystalline product.

mp = 137.5°-138° C.

ms (fd) = 344 (M+), 345 (M$^+$+1)

[α]$_{365}$(CH$_3$OH) = +308.21°

Analysis for C$_{22}$H$_{36}$N$_2$O: Theory: C, 76.69; H, 10.53; N, 8.13 Found: C, 76.51; H, 10.41; N, 8.10

D. Preparation of title compound.

Product from 45 C above (4.83 g), glutaric anhydride (1.60 g), and dry DMF (325 ml) were combined and stirred at room temperature under nitrogen. After 3 hours the mixture was evaporated to dryness to provide 6.44 g of viscous oil. This was passed over a silica column eluting with a solvent gradient of ethyl acetatemethanol (9:1) to ethyl acetate-methanol (1:1). Evaporation of solvent provided 6.30 g of a white foam. This was dissolved in hot ethyl acetate, filtered and evaporated to provide 5.93 g of a white solid.

mp = 107°-110° C.

ms (fd) = 459 (M$^+$+1)

[α]$_{365}$ = +204.82°

Analysis for C$_{27}$H$_{42}$N$_2$O$_4$ Theory: C, 70.71; H, 9.23; N, 6.11 Found: C, 70.47; H, 9.27; N, 6.19

EXAMPLE 46

Preparation of (3R,4R)-(R)-Q-CH$_2$-C(E)H-NH-C(O)(CH$_2$)$_3$CO$_2$H where E is cyclohexylmethyl.

The procedures of Example 45 were followed using the materials indicated below.

A. Preparation of (3R,4R)-(R)Q-C(O)-C(E)H-NH.tBOC

| | |
|---|---|
| Q—H | (2.0 g) |
| (D)HOOC—C(E)H—NH.tBOC | (2.62 g) |
| HOBT | (1.32 g) |
| DCC | (2.01 g) |
| DMF | (145 ml) |
| Product | (3.79 g) | ms (fd) = 458 (M+)

[α]$_{365}$ = +142.29°

Analysis for C$_{27}$H$_{42}$N$_2$O$_4$: Theory: C, 70.71; H, 9.23; N, 6.11 Found: C, 70.85; H, 9.33; N, 6.25

B. Preparation of (3R,4R)-(R)-Q-C(O)-C(E)H-NH$_2$

Product from 46 A (3.75 g)

6N HCl (250 ml)

Methanol (200 ml)

Product (2.43 g) as white crystals mp = 177°-179° C.

ms (fd) = 359 (M$^+$+1)

[α]$_{365}$ = +168.24°

Analysis for C$_{22}$H$_{34}$N$_2$O$_2$: Theory: C, 73.70; H, 9.56; N, 7.81 Found: C, 73.47; H, 9.42; N, 7.62

C. Preparation of (3R,4R)-(R)-Q-CH$_2$-C(E)H-NH$_2$

Product from B (2.43 g) in dry THF (100 ml)

RedAl (10 ml)

Product (1.92 g) as white crystals mp = 175°-176.5° C.

ms (fd) = 345 (M$^+$+1)

[α]$_{365}$ = +182.37°

Analysis for C$_{22}$H$_{36}$N$_2$O: Theory: C, 76.60; H, 10.53; N, 8.13 Found: C, 76.42; H, 10.50; N, 8.04

D. Preparation of (3R,4R)-(R)Q-CH$_2$-C(E)H-NH-C(O)-(CH$_2$)$_3$CO$_2$H

Compound from 46 C above (1.88 g)

Glutaric anhydride (0.571 mg)

Dry DMF (140 ml)

Product (2.16 g)

mp = 92°-95° C.

ms (fd) = 459 (M$^+$+1)

$[\alpha]_{365} = +59.31°$

Analysis for $C_{27}H_{42}N_2O_4$ Theory: C, 70.71; H, 9.23; N, 6.11 Found: C, 70.36; H, 9.33; N, 5.75

EXAMPLE 47

Preparation of (3S,4S)-(S)-Q-CH$_2$C(E)H-NH-C(O)(CH$_2$)$_3$CO$_2$H

The procedure of Example 45 was followed using materials indicated.

A. Preparation of (3S,4S)-(S)-QC(O)C(E)H-NH(tBOC) (3S,4S)-dimethyl-4-(3-hydroxyphenyl)-piperidine (Q-H) (2 g).

| | |
|---|---|
| (L)HOOC—CH(E)—NH(tBOC) | (2.62 g) |
| HOBT | (1.32 g) |
| DCC | (2.01 g) |
| Dry DMF | (145 ml) |
| Product | (4.11 g) | ms (fd) = 258 (M+)
$[\alpha]_{365}(CH_3OH) = -144.55°$

Analysis for $C_{27}H_{42}N_2O_4$: Theory: C, 70.71; H, 9.23; N, 6.11 Found: C, 70.54; H, 9.14; N, 6.09

B. Preparation of (3S,4S)-(S)-QC(O)CH(E)NH$_2$. Product from 47 A above (4.05 g)

| | |
|---|---|
| Product from 47 A above | (4.05 g) |
| 6N HCl | (250 ml) |
| Methanol | (200 ml) |
| Product | (2.58 g) | ms (fd) = 358 (M+), 359 (M+ +1)
$[\alpha]_{365} - 165.78°$

Analysis for $C_{22}H_{34}N_2O_2$: Theory: C, 73.70; H, 9.55; N, 7.81 Found: C, 73.49; H, 9.64; N, 7.65

C. Preparation of (3S,4S)-(S)-Q-CH$_2$-CH(E)-NH$_2$ Product from 47 B (2.34 g) in dry THF (100 ml).
RedAl (10 ml)
Product (1.70 g)
mp = 176°-177° C.
ms (fd) = 344 (M+), 345 (M+ +1)
$[\alpha]_{365} = -180.04°$ Analysis for $C_{22}H_{36}N_2O$: Theory: C, 76.69; H, 10.53; N, 8.13 Found: C, 76.48; H, 10.58; N, 8.03

D. Formation of title compound
Product from 47 C (1.62 g)

| | |
|---|---|
| Product from 47 C | (1.62 g) |
| Glutaric anhydride | (537 mg) |
| Dry DMF | (125 ml) |
| Product | (1.90 g) as white solid | m.p. = 102.5°-104° C.
ms (fd) = 459 (M+ +1)
$[\alpha]_{365} = -54.46°$

Analysis for $C_{27}H_{42}N_2O_4$ Theory: C, 70.71; H, 9.23; N, 6.11 Found: C, 70.41; H, 9.49; N, 5.94

EXAMPLE 48

Preparation of (−)-(3S,4S)-(R)-Q-CH$_2$-CH(E)-NH-C(O)-(CH$_2$)aCO$_2$H where E is cyclohexylmethyl.

The procedure of Example 45 was followed using the materials indicated below.

A. Preparation of (−)-(3S,4S)-(R)-Q-C(O)CH(E)NH(BOC)

| | |
|---|---|
| (−)—(3S,4S)—dimethyl-4-(3-hydroxyphenyl)piperidine-(Q—H) | (2.0 g) |
| (D)HOOC—CH(E)—NH(tBOC) | (2.62 g) |
| HOBT | (1.32 g) |
| DCC | (2.01 g) |
| DMF (dry) | (145 ml) |

Product (3.86 g) as white foam
ms (fd) = 458 (M+)
$[\alpha]_{365}(CH_3OH) = -128.13°$ B. Preparation of (3S,4S)-(R)-Q-C(O)CH(E)NH$_2$
Product from 48 A (3.86 g)
6N HCl (250 ml)
Methanol (200 ml)
Product (2.36 g) as pink foam
ms (fd) = 359 (M+ +1)
$[\alpha]_{365} = -180.58°$ Analysis for $C_{22}H_{34}N_2O_2$: Theory: C, 73.70; H, 9.56; N, 7.81 Found: C, 73.41; H, 9.45; N, 7.41

C. Preparation of (3S,4S)-(R)-Q-CH$_2$-CH(E)NH$_2$
Product from 48 B (2.36 g) in dry toluene (100 ml)
RedAl (10 ml)
Product (1.94 g)
ms (fd) = 345 (M+ +1)
$[\alpha]_{365} = -291.71°$ Analysis for $C_{22}H_{36}N_2O$: Theory: C, 76.69; H, 10.53; N, 8.13 Found: C, 76.51; H, 10.62; N, 8.05

D. Formation of title compound. Product from 48 C above (1.88 g)
Glutaric anhydride (570 mg)
DMF (dry) (140 ml)
Product (2.03 g)
mp = 106°-109° C.
ms (fd) = 459 (M+ +1)
$[\alpha]_{365} = -194.96°$ Analysis for $C_{27}H_{42}N_2O_4$ Theory: C, 70.71; H, 9.23; N, 6.11 Found: C, 71.00; H, 9.33; N, 6.41

In Examples 49-59 the following procedure was used. The reactants were mixed and refluxed under nitrogen with the reaction followed by thin layer chromatography. The reaction was normally complete after about 1 hour. The mixture was evaporated to dryness and the residue partitioned between ethyl acetate and water. The pH of the water layer was adjusted to 9.8 with 1N NaOH. The layers were separated and the organic layer washed with water. After drying over K$_2$CO$_3$, the ethyl acetate was evaporated. The resulting residue was either passed through a silica column eluting with ethyl acetate or passed over a chromatron using a 2 mm plate and eluting with ethyl acetate. Removal of the ethyl acetate provided the product.

In Examples 49-70 "T" represents Q-CH$_2$-CH(E)-NH-C(O)(CH$_2$)$_3$-C(O)- where E is cyclohexylmethyl The indicated configuration refers to the 3 and 4 positions of the piperidine and the other designation refers to the configuration of the asymmetric center in the moiety attached to the nitrogen of the piperidine.

EXAMPLE 49

Preparation of (3S,4S)-(S)-T-OCH$_3$ (3S,4S)-(S)-T-OH (400 mg)
Methanol (20 ml)
Methanol saturated with HCl (20 ml)
Product as the HCl salt (325 mg)
m.p. = 74°-78° C.
$[\alpha]_{365}(CH_3OH) = -62.23°$ Analysis for $C_{28}H_{44}N_2O_4 \cdot HCl$ Theory: C, 66.06; H, 8.91; N, 5.50 Found: C, 66.29; H, 9.11; N, 5.67

EXAMPLE 50

| Preparation of (3R,4R)—(S)—T—OCH₃ | |
|---|---|
| (3R,4R)—(S)—T—OH | (400 mg) |
| Methanol | (20 ml) |
| Methanol saturated with HCl | (20 ml) |
| Product as the HCl salt | (300 mg) | mg = 167°–170' C.
$[\alpha]_{365}(CH_3OH) = +155.83°$
Analysis for $C_{28}H_{44}N_2O_4 \cdot HCl$ Theory: C, 66.06; H, 8.91; N, 5.50 Found: C, 65.81; H, 9.02; N, 5.53

EXAMPLE 51

Preparation of (3S, 4S)-(S)-(T)-OCH₂CH₃
(3S,4S)-(S)-T-OH (300 mg)
Ethanol (20 ml)
Ethanol saturated with HCl (20 ml)
Product as the HCl salt (210 mg)
m.p. = 83°–87° C.
Analysis for $C_{29}H_{46}N_2O_4 \cdot HCl$ Theory: C, 66.58; H, 9.06; N, 5.35 Found: C, 66.84; H, 9.22; N, 5.60

EXAMPLE 52

Preparation of (3R,4R)-(S)-T-OCH₂CH₃
(3R,4R)-(S)-T-OH (400 mg)
Ethanol (20 ml)
Ethanol saturated with HCl (20 ml)
Product as the HCl salt (200 mg)
m.p. = 163°–168° C.
Analysis for $C_{29}H_{46}N_2O_4 \cdot HCl$ Theory: C, 66.58; H, 9.06; N, 5.36 Found C, 66.85; H, 8.80; N, 5.18

EXAMPLE 53

| Preparation of (3S,4S)—(S)—T—O(CH₂)₂CH₃ | |
|---|---|
| (3S,4S)—(S)—T—OH | (300 mg) |
| 1-Propanol | (20 ml) |
| 1-Propanol saturated with HCl | (20 ml) |
| Product as the HCl salt | (215 mg) | m.p. = 75.5°–79° C.
Analysis for $C_{30}H_{48}N_2O_4 \cdot HCl$ Theory: C, 67.08; H, 9.19; N, 5.22 Found: C, 67.31; H, 9.40; N, 5.37

EXAMPLE 54

Preparation of (3R,4R)-(S)-T-O(CH₂)₂CH₃
(3R,4R)-(S)-T-OH (1 g)
1-Propanol (60 ml)
1-Propanol saturated with HCl (60 ml)
Product as the HCl salt (900 mg) as white solid
m.p. = 173°–175° C.
$[\alpha]_{365} = +178.88°$
Analysis for $C_{30}H_{48}N_2O_4 \cdot HCl$ Theory: C, 67.08; H, 9.19; N, 5.21 Found: C, 66.80; H, 9.10; N, 5.05

EXAMPLE 55

Preparation of (3S,4S)-(S)-T-OCH₂CH(CH₃)₂
(3S,4S)-(S)-T-OH (250 mg)
Isobutyl alcohol (20 ml)
Isobutyl alcohol saturated with HCl (20 ml)
Product as the HCl salt (200 mg)
m.p. = 79°–82° C.
Analysis for $C_{31}H_{50}N_2O_4 \cdot HCl$ Theory: C, 67.55; H, 9.33; N, 5.08 Found: C, 67.29; H, 9.55; N, 5.36

EXAMPLE 56

Preparation of (3R,4R)-(S)-T-OCH₂CH(CH₃)₂
(3R,4R)-(S)-T-OH (1 g)
Isobutyl alcohol (60 ml)
Isobutyl alcohol saturated with HCl (60 ml)
Product as the HCl salt (845 mg)
m.p = 168°–172° C.
$[\alpha]_{365} = +176.48°$
Analysis for $C_{31}H_{50}N_2O_4 \cdot HCl$ Theory: C, 67.55; H, 9.33; N, 5.08 Found: C, 67.61; H, 9.40; N, 5.09

EXAMPLE 57

Preparation of (3R,4R)-(S)-T-O(CH₂)₆CH₃
(3R,4R)-(S)-T-OH (300 mg)
Heptyl alcohol (20 ml)
Heptyl alcohol saturated with HCl (20 ml)
Product as the HCl salt (300 mg)
m.p. = 177°–179° C.
$[\alpha]_{365} = +143.48°$
Analysis for $C_{34}H_{56}N_2O_4 \cdot HCl$ Theory: C, 68.83; H, 9.68; N, 4.72 Found: C, 68.57; H, 9.53; N, 4.96

EXAMPLE 58

Preparation of (3S,4S)-(R)-T-OCH₂CH(CH₃)₂
(3S,4S)-(R)=T-OH (360 mg)
Isobutyl alcohol (20 ml)
Isobutyl alcohol saturated with HCl (20 ml)
Product as the HCl salt (270 mg)
m.p. = 178°–180° C.
$[\alpha]_{365} = -170.80°$
Analysis for $C_{31}H_{50}N_2O_4 \cdot HCl \cdot \frac{1}{2}H_2O$ Theory: C, 66.45; H, 9.36; N, 5.00 Found: C, 66.23; H, 9.14; N, 5.18

EXAMPLE 59

Preparation of (3R,4R)-(R)-T-OCH₂CH(CH₃)₂
(3R,4R)-(R)-T-OH (350 mg)
Isobutyl alcohol (20 ml)
Isobutyl saturated with HCl (20 ml)
Product as the HCl salt (270 mg)
m.p. = 81°–84° C.
$[\alpha]_{365} = +46.24°$
Analysis for $C_{31}H_{50}N_2O_4 \cdot HCl$ Theory: C, 67.55; H, 9.33; N, 5.08 Found: C, 67.67; H, 9.23; N, 5.26

The following procedure was used in Examples 60–66. The reactants were mixed together with the DCC added last and stirred at room temperature under nitrogen. After about 24 hours the reaction mixture was filtered and evaporated to dryness. The residue was dissolved in ethyl acetate which was then washed one time with water, dried over $K_2CO_3$ and evaporated. The residue was then either passed over a silica column or over a chromatron using a 2 mm plate. Removal of the solvent provided the product which was then converted to the HCl salt.

EXAMPLE 60

| Preparation of (3S,4S)—(S)—T—OCH₂C(O)NH₂ | |
|---|---|
| (3S,4S)—(S)—T—OH | (400 mg) |
| HOCH₂C(O)NH₂ | (66 mg) |
| HOBT | (118 mg) |
| DCC | (180 mg) |
| DMF dry | (40 ml) |

Product was passed over a chromatron eluting with a gradient of ethyl acetate to ethyl acetate/ethanol (19:1) to provide the free amide product (194 mg).
ms (fd)=515 (M+), 516 (M+ +1)
Product as the HCl salt
m.p. = 110°-116° C.
Analysis for $C_{29}H_{45}N_3O_5 \cdot HCl \cdot \frac{1}{2}H_2O$ Theory: C, 62.06; H, 8.44; N, 7.48 Found: C, 62.11; H, 8.52; N, 7.24

EXAMPLE 61

| Preparation of (3R,4R)—(S)—T—OCH$_2$C(O)NH$_2$ | |
| --- | --- |
| (3R,4R)—(S)—T—OH | (400 mg) |
| HOCH$_2$C(O)NH$_2$ | (66 mg) |
| HOBT | (118 mg) |
| DCC | (180 mg) |

Reaction product was passed over a silica column eluting with a gradient of ethyl acetate to ethyl acetate/methanol (9:1). The recovered material was then passed over a chromatron eluting with a gradient of ethyl acetate to ethyl acetate/ethanol (19:1) to provide the free amide product.
ms (fd)=515 (M+), 516 (M +1)
Conversion of the amide to the HCl salt provided 130 mg of material.
m.p.=103°-106° C.
Analysis for $C_{29}H_{45}N_3O_5 \cdot HCl$ Theory: C, 63.08, H, 8.40; N, 7.61 Found: C, 63.40; H, 8.64; N, 7.32

EXAMPLE 62

| Preparation of (3S,4S)—(S)—T—OCH$_2$C(O)NHCH$_3$ | |
| --- | --- |
| (3S,4S)—(S)—T—OH | (400 mg) |
| HOCH$_2$C(O)NHCH$_3$ | (78 mg) |
| HOBT | (118 mg) |
| DCC | (180 mg) |
| DMF dry | (40 ml) |

The reaction residue was passed over a silica column eluting with ethyl acetate to provide the free amide product (170 mg).
ms (fd)=530 (M+ +1)
The amide was converted to the HCl salt (156 mg) m.p.=67°-71° C.
Analysis for $C_{30}H_{47}N_3O_5 \cdot HCl$ Theory: C, 63.64; H, 8.54; N, 7.42 Found: C, 63.41; H, 8.56; N, 7.59

EXAMPLE 63

| Preparation of (3R,4R)—(S)—T—OCH$_2$C(O)NHCH$_3$ | |
| --- | --- |
| (3R,4R)—(S)—T—OH | (400 mg) |
| HOCH$_2$C(O)NHCH$_3$ | (78 mg) |
| HOBT | (118 mg) |
| DCC | (180 mg) |
| DMF dry | (40 ml) |

The reaction residue was passed over a silica column eluting with ethyl acetate. Removal of solvent provided the product amide. (160 mg).
ms (fd)=530 (M+ +1)
The amide was converted to the HCl salt (140 mg) m.p.=97°-100° C.
Analysis for $C_{30}H_{47}N_3O_5 \cdot HCl$ Theory: C, 63.64; H, 8.54; N, 7.42 Found: C, 63.92; H, 8.49; N, 7.19

EXAMPLE 64

| Preparation of (3R,4R)—(S)—T—OCH$_2$C(O)N(CH$_3$)$_2$ | |
| --- | --- |
| (3R,4R)—(S)—T—OH | (550 mg) |
| HOCH$_2$C(O)N(CH$_3$)$_2$ | (124 mg) |
| HOBT | (162 mg) |
| DCC | (247 mg) |
| DMF dry | (50 ml) |

The reaction residue was passed over a silica column eluting with a gradient of ethyl acetate to ethyl acetate/methanol (1:1) providing the free amide (206 mg) as a yellow foam.
ms (fd)=544 (M+)
The amide was converted to the HCl salt (178 mg) m.p.=80°-83° C.
Analysis for $C_{31}H_{49}N_3O_5 \cdot HCl \cdot H_2O$ Theory: C, 62.23; H, 8.76; N, 7.03 Found: C, 61.93; H, 8.45; N, 7.30

EXAMPLE 65

| Preparation of (3S,4S)—(S)—T—OCH$_2$C(O)NHCH$_2$CH$_3$ | |
| --- | --- |
| (3S,4S)—(S)—T—OH | (400 mg) |
| HOCH$_2$C(O)NHCH$_2$CH$_3$ | (90 mg) |
| HOBT | (118 mg) |
| DCC | (180 mg) |
| DMF dry | (40 ml) |

The residue was passed over a silica column eluting with ethyl acetate and then passed over chromatron eluting with ethyl acetate-ethanol (19:1) to provide a viscous oil (145 mg).
ms (fd)=544 (M+ +1)
This material was converted to the HCl salt (140 mg).
m.p.=89°-93° C.
Analysis for $C_{31}H_{49}N_3O_5 \cdot HCl$ Theory: C, 64.17; H, 8.69; N, 7.24 Found: C, 64.45; H, 8.73; N, 7.36

EXAMPLE 66

| Preparation of (3R,4R)—(S)—T—OCH$_2$C(O)NHCH$_2$CH$_3$ | |
| --- | --- |
| (3R,4R)—(S)—T—OH | (400 mg) |
| HOCH$_2$C(O)NHCH$_2$CH$_3$ | (90 mg) |
| HOBT | (118 mg) |
| DCC | (180 mg) |
| DMF dry | (40 ml) |

The residue was passed over a silica column eluting with a gradient of ethyl acetate to ethyl acetatemethanol (9:1). The recovered material was passed over a chromatron eluting with a gradient of ethyl acetate to ethyl acetate-ethanol (19:1) to provide a viscous oil (146 mg).
ms (fd)=544 (M+ +1)
This material was converted to the HCl salt (135 mg).
m.p.=84°-87° C.
Analysis for $C_{31}H_{49}N_3O_5 \cdot HCl \cdot H_2O$ Theory: C, 62.23; H, 8.76; N, 7.02 Found C, 62.17; H, 8.74; N, 6.86

EXAMPLE 67

Preparation of (3R,4R)-(S)-T-OCH(CH$_3$)OC(O)CH$_3$
(3R,4R)-(S)-T-OH (687 mg)
BrCH(CH$_3$)OC(O)CH$_3$ (926 mg) in CH$_2$Cl$_2$ (100 ml)
K$_2$CO$_3$ (1.89 g)
The above reagents were mixed together at room temperature and stirred overnight. The mixture was filtered and then evaporated to dryness to provide a black oil (725 mg). This material was passed through a silica column eluting with a gradient of ethyl acetate to ethyl acetate-methanol (1:1). Removal of solvent provided a yellow foam (200 mg).

ms (fd)=545 (M+)

This material was converted to the HCl salt and dried at 60° C. to provide a tan solid (170 mg).

m.p.=142°-146° C.

Analysis for $C_{31}H_{48}N_2O_6 \cdot HCl \cdot \frac{1}{2}H_2O$ Theory: C, 63.08; H, 8.54; N, 4.75 Found: C, 62.82; H, 8.33; N, 4.79

EXAMPLE 68

Preparation of (3R,4R)-(S)-T-O-G where is G is 4-methoxycyclohexyl (3R,4R)-(S)-T-OH (463 mg) and $K_2CO_3$ (1.83 g) were combined with DMF (70 ml) and heated to 70°–80° C. At this temperature $C_6H_5SO_2O$-G (1.52 g) was added and the mixture stirred an additional 20 hours at 70°–80° C. The mixture was cooled to room temperature, filtered and evaporated to dryness. The residue was partitioned between ethyl acetate and water. The water layer was adjusted to a pH of 9.8 with 1N NaOH and the layers separated. The ethyl acetate layer was washed one time with water, dried over $K_2CO_3$ and evaporated to dryness to provide a residue (900 mg). This material was passed over a silica column eluting with ethyl acetate.

Removal of solvent provided 400 mg of material which was converted to the HCl salt (355 mg).

m.p.=169°-172° C.

Analysis for $C_{34}H_{54}N_2O_5 \cdot HCl$ Theory: C, 67.24; H, 9.13; N, 4.61 Found: C, 67.01; H, 9.14; N, 4.84

EXAMPLE 69

Preparation of (3S,4S)-(S)-T-O-G where G is 4-methoxycyclohexyl

The procedure of Example 68 was followed using the following materials:

(3S,4S)-(S)-T-OH (463 mg)
p-$CH_3C_6H_5SO_2$-O-G (1.52 g)
$K_2CO_3$ (1.83 g)
DMF (70 m)

The reaction residue was passed over a silica column eluting with ethyl acetate to provide a white foam (450 mg).

ms (fd)=570 (M+), 571 (M++1)

This material was converted to the HCl salt and dried at 60° C. to provide 395 mg of product.

m.p.=86°-90° C.

Analysis for $C_{34}H_{54}N_2O_5 \cdot HCl$ Theory: C, 67.25; H, 9.13; N, 4.61 Found: C, 67.08; H, 9.09; N, 4.85

EXAMPLE 70

Preparation of (3R,4R)-(S)-T-O-J where J is

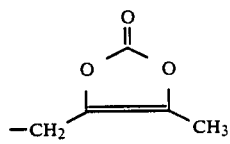

Under a nitrogen atmosphere J-Br (720 mg) in dry $CH_2Cl_2$ (100 ml) was added dropwise to (3R,4R)-(S)-T-OH (458 mg) and $K_2CO_3$ (1.27 g) at 0° C. The mixture was allowed to warm to room temperature and stirred for one hour. The mixture was filtered and the liquid phase evaporated to dryness to provide a residue (600 mg). This material was passed over a silica column eluting with a gradient of ethyl acetate to ethyl acetatemethanol (9:1). Removal of solvent provided a white solid which was recrystallized from ethyl acetate (210 mg).

m.p.=145°-147° C.

ms (fd)=537 (M++1)

This material was converted to the HCl salt and dried at 60° C. to provide a white solid (185 mg).

m.p.=137°-141° C.

Analysis for $C_{32}H_{46}N_2O_7 \cdot HCl \cdot H_2O$ Theory C, 61.47; H, 7.90; N, 4.48 Found: C, 61.83; H, 7.98; N, 4.69.

EXAMPLE 71

Preparation of B-C(O)$(CH_2)_2$C(O)OCH$_2$CH$_3$ where B is (tran3)-Q-$(CH_2)_2$N(cyclohexyl)-(Prep XII)

| | |
|---|---|
| B—H | (600 mg) |
| HOC(O)$CH_2CH_2$C(O)OCH$_2$CH$_3$ | (264 mg) |
| HOBT | (244 mg) |
| DCC | (373 mg) |
| DMF dry | (50 ml) |

The above reactants were mixed together (DCC added last) and stirred at room temperature under nitrogen. After 24 hours the reaction mixture was filtered and the filtrate was evaporated to dryness. The residue was dissolved in ethyl acetate which was washed once with water, dried over $K_2CO_3$ and evaporated to provide a residue (1.09 g). The residue was passed over a silica column eluting with a gradient of hexane/ethyl acetate (9:1) to ethyl acetate. Removal of solvent provided 570 mg of material. This was passed over a 2 mm plate on a chromatron eluting with ethyl acetate. Removal of the solvent provided a viscous oil (470 mg).

ms (fd)=459 (M++1)

This material was converted to the HCl salt and dried to provide a solid (450 mg).

m.p.=96°-100° C.

Analysis for $C_{27}H_{42}N_2O_4 \cdot HCl \cdot \frac{1}{2}H_2O$ Theory: C, 64.32; H, 8.80; N, 5.56; Found: C, 64.22; H, 8.85; N, 5.56.

EXAMPLE 72

Preparation of B-C(O)$(CH_2)_2$C(O)OCH$_2$CH(CH$_3$)$_2$ where B is as defined in Example 71. The procedure of Example 71 was followed using B-H (600 mg) prepared as in Preparation XII.

HOC(O)$(CH_2)_2$C(O)OCH$_2$CH(CH$_3$)$_2$(315 mg)
HOBT (244 mg)
DCC (373 mg)
DMF dry (40 ml)

The residue was passed over a silica column eluting with a gradient of hexane/ethyl acetate (9:1) to ethyl acetate. The recovered material was put over a 2 mm plate on a chromatron eluting with ethyl acetate to provide a white foam (380 mg).

ms (fd)=487 (M++1)

This material was converted to the HCl salt and dried.

m.p.=82°-86° C.

Analysis for $C_{29}H_{46}N_2O_4 \cdot HCl$ Theory: C, 66.58; H, 9.06; N, 5.36; Found: C, 66.18; H, 8.89; N, 5.12.

EXAMPLE 73

Preparation of B-C(O)$(CH_2)_2$C(O)OCH$_2$($C_6H_{11}$) where B is defined in Example 71 and $C_6H_{11}$ is cyclohexyl.

| | |
|---|---|
| B—H prepared as in Preparation XII | (600 mg) |
| HOC(O)(CH$_2$)$_2$C(O)OCH$_2$(C$_6$H$_{11}$) | (387 mg) |
| HOBT | (244 mg) |
| DCC | (373 mg) |
| DMF dry | (40 ml) |

The residue was passed over a silica column eluting with a gradient of hexane/ethyl acetate (9:1) to ethyl acetate. The recovered material was then passed over a 2 mm plate on a chromatron eluting with ethyl acetate to provide a viscous oil (370 mg).

ms (fd) = 526 (M+), 527 (M+ +1)

This material was converted to the HCl salt and dried.

m.p. = 79°-84° C.

Analysis for C$_{32}$H$_{50}$N$_2$O$_4$.HCl Theory: C, 68.24; H, 9.13; N, 4.97; Found: C, 67.85; H, 9.42; N, 4.93.

The instant compounds are useful in blocking peripherial opioid receptors and preventing peripherally opiate induced side effects. These side effects induced by the administration of an opiate such as morphine to a mammal can include constipation, nausea, and vomiting. These compounds can also be useful in the treatment of irritable bowel syndrome and idiopathic constipation. While not wishing to be bound by the theory, it is believed that the instant compounds act as opioid antagonists and bind to peripherial opioid receptors outside of the brain. The compounds do not substantially pass through the blood-brain barrier and therefore do not mitigate the opioid's effect on central (brain and spinal cord) opioid receptors.

In order to determine in vivo opioid receptor antagonism, the mouse writhing analgesis test was used. Test compounds were measured for their ability to block morphine-induced analgesis.

Five CF-1 male mice (Charles River, Portage, MI), weighing approximately 20 g after being fasted overnight, were observed simultaneously for the writhing response. The writhing response was defined as a contraction of the abdominal musculature, followed by the extension of the hind limbs, and was induced by the intraperitoneal administration of 0.6% acetic acid in a volume of 1 ml/100 g body weight. The observation period was 10 min. in duration, beginning 5 min. after injection of acetic acid. The percent inhibition of writhing was calculated from the average number of writhes in the control (non-drug) group. Each data point is the mean (±standard error) for five mice. The ED$_{50}$ was defined as the dose of agonist that inhibited mean writhing by 50%. The AD$_{50}$ was defined as the dose of antagonist that reduced the inhibition of writhing produced by a 1.25 mg/kg dose of morphine sulfate to 50%. Each mouse was only used once. All drugs were administered subcutaneously (1 ml/100 g bwt) 20 min. before the injection of acetic acid.

Determinations of peripheral opioid activity were conducted. Mice maintained (6 mice/cage) on 0.01 M saccharin water with 1 g/1 morphine sulfate for a minimum of 10 days with mice averaging 3.0 +g water/mouse/day for at least three days are used as subjects. The morphine water was removed 45 min. prior to injection with the proposed opioid antagonist. Initial testing consisted of 5 mice/dose of compound. The antagonist was given by the subcutaneous or oral, route of administration, and the mice were placed in 11-14"×4 7/12 I.D. clear plastic cylinders with white paper towels used for a floor.

The mice were then monitored visually for 30 minutes post-injection for the presence of jumping and of diarrhea. Jumping was scored as positive if at least one jump occurred in 30 min. Diarrhea was scored as positive when feces were moist enough to stain the white paper at the base of the cylinder. After 30 minutes of testing, the mice were placed back in original cages, put back on morphine water, and not tested again for 48 hrs. Lower doses of the antagonist compounds were tested until threshold doses for diarrhea were determined. Diarrhea is a peripherally mediated sign of precipitated opiate abstinence.

The extent of the effect on peripheral activity compared to central activity of the present compounds can be determined by comparing the AD$_{50}$ for the mouse writhing test with the ED$_{50}$ for the mouse diarrhea test. The higher the ratio, the greater the relative antagonism of the peripheral opioid receptors by a particular compound. This ratio for each compound is provided in Table I.

TABLE I

| Example No.[1] | AD$_{50}$[2] | ED$_{50}$[3] | Ratio[4] |
|---|---|---|---|
| 1 | >40 | 0.01 | >4000 |
| 2A | 8.4 | 0.29 | 29 |
| 2B | 10.2 | 0.19 | 54 |
| 3A | 14.2 | 0.16 | 89 |
| 3B | 15.5 | 0.14 | 111 |
| 4 | 17.5 | 0.07 | 250 |
| 5 | >20 | 0.012 | >1666 |
| 6 | 30 | 0.07 | 428 |
| 7 | 8.62 | 0.45 | 19 |
| 8 | >1.25 | 0.64 | >2 |
| 9 | >1.25 | 0.25 | >5 |
| 10 | 9.3 | 0.12 | 78 |
| 11 | 12.4 | 0.30 | 41 |
| 12 | 20 | 0.20 | 100 |
| 13 | >40 | 0.29 | >138 |
| 14 | 21 | 0.32 | 656 |
| 15 | 1.39 | 0.028 | 50 |
| 16 | >20 | 0.12 | >166 |
| 17 | >40 | 3.28 | >12 |
| 18 | 1.31 | 0.30 | 4.5 |
| 19 | 6.3 | 0.082 | 77 |
| 20 | 2.1 | 0.06 | 35 |
| 21 | 17.1 | 0.073 | 71 |
| 22 | 1.25 | 0.016 | 63 |
| 23 | >1.25 | 0.24 | >5 |
| 24 | 19.2 | 0.62 | 31 |
| 25 | 0.61 | 0.06 | 10 |
| 26 | 3.6 | 0.05 | 72 |
| 27 | 11 | 0.18 | 61 |
| 28 | >1.25 | 0.10 | >12 |
| 29 | 7.6 | 0.99 | 7.7 |
| 30 | 12.4 | <0.30 | >40 |
| 31 | >40 | 0.19 | >200 |
| 32 | 9.4 | 0.16 | 59 |
| 33 | 3.67 | 0.03 | 122 |
| 34 | 8.2 | 0.39 | 21 |
| 35 | >1.25 | 0.42 | >3 |
| 36 | 2.9 | 0.39 | 8 |
| 37 | 12.8 | 0.05 | 256 |
| 38 | 28.9 | 0.018 | 1605 |
| 39 | 5.1 | 0.05 | 102 |
| 40 | 2.20 | 0.74 | 3 |
| 41 | 32 | 0.43 | 74 |
| 42 | >20 | 0.12 | >160 |
| 43 | >10 | <1.0 | >10 |
| 44 | >2 | 0.07 | >30 |
| 45D | >40 | 0.029 | >1379 |
| 46D | 6.5 | 0.09 | 72 |
| 47D | >40 | 0.01 | >4000 |
| 48D | >40 | 0.05 | >800 |
| 49 | 9.9 | >10 | >1 |
| 50 | 20 | 0.056 | 357 |

TABLE I-continued

| Example No.[1] | AD$_{50}$[2] | ED$_{50}$[3] | Ratio[4] |
|---|---|---|---|
| 51 | >40 | | |
| 52 | 28 | 0.02 | 1400 |
| 53 | >40 | 1.06 | >38 |
| 54 | 27 | 0.0015 | 18000 |
| 55 | >40 | 0.05 | >800 |
| 56 | >40 | 0.002 | 20000 |
| 57 | >40 | 0.068 | >588 |
| 58 | >40 | 0.17 | >235 |
| 59 | >40 | 0.059 | >678 |
| 60 | >10 | 0.035 | >285 |
| 61 | 22 | 0.13 | 169 |
| 62 | >40 | 0.03 | >1333 |
| 63 | 12 | 0.003 | 4000 |
| 64 | 13.5 | | |
| 65 | >40 | 0.02 | >2000 |
| 66 | 12.2 | 0.005 | 2440 |
| 67 | >40 | | |
| 68 | 18.8 | 0.29 | 65 |
| 69 | >40 | 0.03 | >1333 |
| 70 | 18.2 | 0.017 | 1070 |
| 71 | 3.71 | 0.29 | 13 |
| 72 | 5.5 | 0.017 | 324 |
| 73 | 9.2 | 0.17 | 54 |

[1] compounds tested correspond to example number
[2] mg/kg in mouse writhing test
[3] mg/kg in mouse diarrhea test
[4] ratio of AD$_{50}$ to ED$_{50}$ The compounds of the present invention have been found to display excellent activity in an opioid receptor binding assay which measures the affinity of the compounds to to bind to mu receptors. This assay was conducted by the following procedure.

Male Sprague Dawley rats for mu site experiments were sacrificed via decapitation and the brains were removed. The brain tissue, rat whole brain minus cerebellum for mu was homogenized in a Teflon and glass tissue homogenizer. A supernatant I, pellet IV, fraction was frozen in a nitrogen freezer at 1.33 g/ml concentration and stored for not longer than five weeks prior to use. Pellets were rehydrated with physiological buffer prior to use.

For mu sites increasing concentrations of experimental compound, [0.1 to 1000 nanomolar (nM)], Kreb-Hepes buffer pH 7.4, and tritiated naloxone (0.5 nM) ($^3$H ligand) were combined in polystyrene tubes at room temperature. The reaction was initiated by the addition of the resuspended tissue which had been preincubated at 37° C. for 20 minutes. The reaction mixture was incubated in a 37° C. water bath for 20 minutes. The reaction was terminated by rapid filtration, (Brandel Cell Harvestor), through Whatman GF/B glass filters that had been presoaked in Krebs-Hepes buffer pH 7.4. The filters were then washed 2x with 5 ml of ice cold Krebs-Hepes buffer pH 7.4. Washed filters were placed in scintillation vials and 10 ml RedySolv, (Brandel), was added and samples counted in a Searle D-300 beta counter. Means and standard error statistics were calculated for triplicate experimental determinations in certain cases. The incubation time for the reaction mixture was 20 minutes at 37° C.

$K_i$ values were calculated using a minitab statistical program according to the following formula:

$$K_i = \frac{IC_{50}}{1 + \frac{\text{concentration of }^3\text{H ligand}}{K_D}}$$

wherein IC$_{50}$ is the concentration at which 50% of the $^3$H ligand is displaced by the test compounds and K$_D$ is the dissociation constant for the $^3$H ligand at the receptor site. K$_D$ can be determined as described by Bennett, "Methods in Binding Studies", *Neurotransmitter Receptor Binding*, Yamamura, et al., ed., p. 57-90, Raven Press, N.Y. (1978) incorporated herein by reference.

The results of the evaluation of certain compounds of the present invention in the opioid receptor binding assay are set forth below in Table II. In the Table, column 1 sets forth the Example Number of the compound evaluated, column 2 and 3, the Ki value in nanomolar (nM) at the mu receptor and columns 3 and 4 the percent displacement by the test compound at the indicated concentration, ie., 10 nm or 100 nm.

TABLE II

Naloxone [$^3$H] Binding Assay (mu receptor)

| Example | Ki[1] | 10 nM[2] | 100 nM[2] |
|---|---|---|---|
| 1 | 6.88 | 72 | 94 |
| 2A | 0.64 | 98 | 100 |
| 2B | 1.20 | 93 | 99 |
| 3A | 0.30 | 100 | 100 |
| 3B | 0.86 | 93 | 99 |
| 4 | 1.41 | 86 | 94 |
| 5 | 0.30 | 100 | 100 |
| 6 | 6.49 | 82 | 94 |
| 7 | 0.63 | 99 | 100 |
| 8 | 0.68 | 95 | 99 |
| 9 | 1.33 | 92 | 100 |
| 10 | 1.46 | 61 | 94 |
| 11 | — | 36 | 80 |
| 12 | — | 43 | 87 |
| 13 | — | 24 | 72 |
| 14 | 32.40 | 20 | 64 |
| 15 | 2.96 | 80 | 99 |
| 16 | 0.96 | 97 | 100 |
| 17 | — | 38 | 82 |
| 18 | 0.63 | 86 | 100 |
| 19 | — | 48 | 92 |
| 20 | 0.74 | 95 | 99 |
| 21 | — | 53 | 80 |
| 22 | 3.59 | 51 | 93 |
| 23 | 4.38 | 77 | 100 |
| 24 | — | 48 | 89 |
| 25 | 1.18 | 77 | 93 |
| 26 | 1.91 | 73 | 100 |
| 27 | 8.00 | 63 | 93 |
| 28 | — | 67 | 100 |
| 29 | — | 56 | 88 |
| 30 | 11.00 | 79 | 96 |
| 31 | 2.52 | 82 | 97 |
| 32 | — | 40 | 100 |
| 33 | 0.26 | 83 | 99 |
| 34 | — | 77 | 91 |
| 35 | 2.15 | 80 | 99 |
| 36 | 3.01 | 85 | 99 |
| 37 | 0.61 | 88 | 100 |
| 38 | 2.98 | 79 | 98 |
| 39 | 0.22 | 100 | 99 |
| 40 | 1.16 | 87 | 100 |
| 41 | 2.45 | 87 | 99 |
| 42 | — | 44 | 89 |
| 43 | — | 59 | 97 |
| 44 | 2.34 | 63 | 85 |
| 45D | 0.56 | 82 | 94 |
| 46D | — | 48 | 84 |
| 47D | 1.55 | 85 | 95 |
| 48D | — | 30 | 78 |
| 49 | 8.19 | 83 | 97 |
| 50 | 3.24 | 87 | 99 |
| 51 | — | 73 | 97 |
| 52 | 2.34 | 87 | 96 |
| 53 | — | 50 | 88 |
| 54 | 5.07 | 81 | 96 |
| 55 | — | 40 | 86 |
| 56 | — | 61 | 92 |
| 57 | — | 0 | 9 |
| 58 | — | 0 | 38 |
| 59 | — | 6 | 53 |

TABLE II-continued

| Example | Naloxone [³H] Binding Assay (mu receptor) | | |
|---|---|---|---|
| | $K_i^{(1)}$ | 10 nM$^{(2)}$ | 100 nM$^{(2)}$ |
| 60 | 5.96 | 76 | 95 |
| 61 | 2.86 | 88 | 97 |
| 62 | — | 70 | 96 |
| 63 | 2.13 | 87 | 99 |
| 64 | 1.51 | 81 | 94 |
| 65 | — | 67 | 93 |
| 66 | 1.84 | 81 | 94 |
| 67 | — | 73 | 95 |
| 68 | — | 68 | 95 |
| 69 | — | 37 | 83 |
| 70 | 1.78 | 89 | 99 |
| 71 | 3.85 | 78 | 96 |
| 72 | — | 73 | 96 |
| 73 | — | 46 | 88 |

(1) In nanomoles
(2) % displacement

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed an excipient which can be a carrier, or a diluent or be diluted by a carrier, or enclosed within a carrier which can be in the form of a capsule, sachet, paper or other container. When the carrier serves as a diluent, it can be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable excipients, include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can also include wetting agents, emulsifying and suspending agents, preserving agents, sweetening agents or flavoring agents. The formulations of the invention can be formulated so as to provide quick, sustained, or delayed release of the active ingredient after administration to the patient by employing procedures well known in the art.

For oral administration, a compound of this invention is preferably admixed with one or more excipients, and molded into tablets or enclosed in gelatin capsules.

The compositions are preferably formulated in a unit dosage form, each dosage containing from about 1 to about 500 mg more usually about 5 to 300 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

In order to more fully illustrate the operation of this invention, the following formulation examples are provided. The samples are illustrative only, and are not intended to limit the scope of the invention. The formulations may employ as active compounds any of the compounds of the present invention.

Formulation 1

Hard gelatin capsules are prepared using the following ingredients:

| | Amount Per Capsule | Concentration by Weight (percent) |
|---|---|---|
| N-(1,4-dioxo-4-((2-(4-(3-hydroxyphenyl)-3,4-dimethyl-1-piperidinyl)-ethyl)-phenylamino)butyl)-leucine monohydrochloride monohydrate (Example 39) | 250 mg | 55.0 |
| starch dried | 200 mg | 43.0 |
| magnesium stearate | 10 mg | 2.0 |
| | 460 mg | 100.0 |

The above ingredients are mixed and filled into hard gelatin capsules in 460 mg quantities.

Formulation 2

Capsules each containing 20 mg of medicament are made as follows:

| | Amount Per Capsule | Concentration by Weight (percent) |
|---|---|---|
| 4-[(3-(4-(3-hydroxyphenyl)-3,4-dimethyl-1-piperidinyl)-1-(cyclohexylmethyl)-propyl)-amino]-4-oxobutanoic acid monohydrate (Example 1) | 20 mg | 10.0 |
| starch | 89 mg | 44.5 |
| microcrystalline cellulose | 89 mg | 44.5 |
| magnesium stearate | 2 mg | 1.0 |
| | 200 mg | 100.0 mg |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| | Amount Per Capsule | Concentration by Weight (percent) |
|---|---|---|
| 5-[[1-(2-methylpropyl)-3-[4-(3-hydroxyphenyl)-3,4-dimethyl-1-piperidinyl]-propyl]amino]-5-oxopentanoic acid (Example 4) | 100 mg | 30.00 |
| polyoxyethylene sorbitan monooleate | 50 mg | 0.02 |
| starch powder | 250 mg | 69.98 |
| | 350.05 mg | 100.00 |

The above ingredients are thoroughly mixed and placed in an empty gelatin capsule.

Formulation 4

Tablets each containing 10 mg of active ingredient are prepared as follows:

| | Amount Per Tablet | Concentration by Weight (percent) |
|---|---|---|
| N-(3-(trans-4-(3-hydroxyphenyl)-3,4-dimethyl-1-piperidinyl)-1-phenylpropyl)-acetamide (Example 6) | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°-60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formula may be prepared using the ingredients below:

| | Amount Per Capsule | Concentration by Weight (percent) |
|---|---|---|
| [2-(trans-4-(3-hydroxyphenyl)-3,4-dimethyl-1-piperidinyl)-1-phenylmethyl-ethyl-amino]-4-oxobutanoic acid (Example 14) | 250 mg | 38.0 |
| cellulose microcrystalline | 400 mg | 60.0 |
| silicon dioxide fumed | 10 mg | 1.5 |
| stearic acid | 5 mg | 0.5 |
| | 665 mg | 100.0 |

The components are blended and compressed to form tablets each weighing 665 mg.

Formulation 6

Suspensions each containing 5 mg of medicament per 5 ml dose are made as follows:

| | per 5 ml of suspension |
|---|---|
| 4-(cyclohexyl-(2-(trans-4-(3-hydroxyphenyl)-3,4-dimethyl-1-piperidinyl)ethyl)amino)-4-oxobutanoic acid propyl ester (Example 31) | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| | Concentration by Weight (percent) |
|---|---|
| 5-(cyclohexyl-(3-trans-4-(3-hydroxyphenyl)-3,4-dimethyl-1-piperidinyl)propyl)amino)-5-oxopentanoic acid ethyl ester monohydrochloride (Example 33) | 0.25 |
| ethanol | 29.75 |
| Propellant 22 (chlorodifluoromethane) | 70.00 |
| | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

What is claimed is:

1. An intermediate which is a trans-3,4-stereoisomer of the compound of the formula

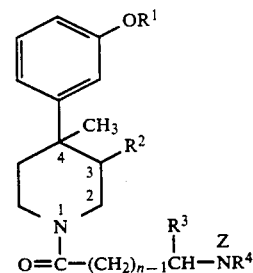

wherein
R$^1$ is hydrogen or (C$_1$-C$_5$)alkyl;
R$^2$ is hydrogen, (C$_1$-C$_5$)alkyl, or (C$_2$-C$_6$)alkenyl;
R$^3$ is hydrogen, (C$_1$-C$_{10}$)alkyl, (C$_3$-C$_{10}$)alkenyl, (C$_3$-C$_8$)cycloalkyl, (C$_3$-C$_8$) cycloalkyl-(C$_1$-C$_3$) alkyl, phenyl, (C$_5$-C$_8$) cycloalkenyl, (C$_5$-C$_8$)cycloalkenyl-(C$_1$-C$_3$)alkyl, or phenyl-(C$_1$-C$_3$) alkyl;
R$^4$ is hydrogen, (C$_3$-C$_8$) cycloalkyl, (C$_1$-C$_{10}$) alkyl, (C$_3$-C$_{10}$)alkenyl, (C$_3$-C$_8$)cycloalkyl-(C$_1$-C$_3$)alkyl, phenyl or phenyl-(C$_1$-C$_3$) alkyl;
Z is an amino blocking group when R$^4$ is not phenyl or Z is hydrogen when R$^4$ is phenyl; and
n is 1-3.

2. The compound of claim 1 wherein $R^2$ is $(C_1-C_5)$alkyl; $R^3$ is $(C_5-C_6)$cycloalkyl, $(C_1-C_5)$alkyl, $(C_5-C_6)$cycloalkyl-$(C_1-C_2)$alkyl, phenyl, or phenyl-$(C_1-C_2)$alkyl; $R^4$ is hydrogen; and Z is an amino blocking group.

3. The compound of claim 1 wherein $R^3$ is phenyl, phenyl$(C_1-C_3)$alkyl, $(C_1-C_{10})$alkyl, $(C_3-C_8)$cycloalkyl, or $(C_3-C_8)$cycloalkyl-$(C_1-C_3)$alkyl; $R^4$ is hydrogen, $(C_3-C_8)$cycloalkyl, $(C_1-C_{10})$alkyl, $(C_3-C_8)$cycloalkyl-$(C_1-C_3)$alkyl, phenyl or phenyl-$(C_1-C_3)$alkyl.

4. The compound of claim 1 wherein $R^3$ is $(C_1-C_5)$alkyl, $(C_5-C_6)$cycloalkyl, $(C_5-C_6)$cycloalkyl-$(C_1-C_3)$alkyl, phenyl, phenyl-$(C_1-C_2)$alkyl, $(C_3-C_{10})$alkenyl, or $(C_5-C_8)$cycloalkenyl.

5. The compound of claim 3 wherein $R^3$ is $(C_5-C_6)$cycloalkyl$(C_1-C_3)$alkyl, phenyl, or phenyl-$(C_1-C_2)$alkyl.

6. The compound of claim 4 wherein $R^4$ is hydrogen, $(C_3-C_8)$cycloalkyl, or phenyl.

7. The compound of claim 6 wherein $R^4$ is hydrogen, or $(C_3-C_8)$cycloalkyl.

8. The compound of claim 4 wherein n is 1 or 2.

9. The compound of claim 8 wherein $R^1$ is $(C_1-C_5)$alkyl.

10. The compound of claim 8 wherein $R^1$ is hydrogen.

11. The compound of claim 10 wherein $R^2$ is $(C_1-C_2)$alkyl; $R^3$ is cyclohexylmethyl or cyclohexyl.

12. The compound of claim 10 wherein $R^4$ is hydrogen or cyclohexyl.

13. The compound of claim 12 wherein $R^4$ is cyclohexyl.

14. The compound of claim 13 wherein n is 2.

15. The compound of claim 2 wherein Z is tert-butyloxycarbonyl or benzyloxycarbonyl.

16. The compound of claim 15 wherein $R^3$ is $(C_5-C_6)$cycloalkyl$(C_1-C_2)$alkyl.

17. The compound of claim 16 wherein $R^3$ is cyclohexylmethyl.

18. The compound of claim 15 wherein $R^3$ is phenyl or phenyl-$(C_1-C_2)$alkyl.

* * * * *